United States Patent [19]
Eichner et al.

[11] Patent Number: 5,935,819
[45] Date of Patent: *Aug. 10, 1999

[54] PROCESS FOR PRODUCING A PHARMACEUTICAL PREPARATION OF PDGF-AB

[76] Inventors: Wolfram Eichner, Richard Wagner Str. 12, Butzbach, Germany, D-35510; Volker Achterberg, Eimsbütterler Marktplatz 11, Hamburg, Germany, D-20257; Albrecht Dorschner, Hogenfelder Kamp 10, Hamburg, Germany, D-22457; Wolfgang Meyer-Ingold, Am Hasenkamp 29, Hamburg, Germany, D-22457; Heiko Mielke, Fischbeker Strasse 22, Neu Wolmstorf, Germany, D-21629; Wilhem Dirks, Bultenweg 13, Braunschweig, Germany, D-38106; Manfred Wirth, Markstrasse 1, Wolfenbuttel, Germany, D-38300; Hansjörg Hauser, Georg-Westermannallee 29, Braunschweig, Germany, D-38104

[ * ] Notice: This patent is subject to a terminal disclaimer.

[21] Appl. No.: 08/778,275

[22] Filed: Jan. 2, 1997

Related U.S. Application Data

[63] Continuation of application No. 08/387,845, filed as application No. PCT/EP93/02295, Aug. 26, 1993, Pat. No. 5,665,567.

[30] Foreign Application Priority Data

Aug. 27, 1992 [DE] Germany ............................ 42 28 457

[51] Int. Cl.$^6$ ............................ C12N 15/16; C12N 15/06; C12N 15/63; A61K 38/18
[52] U.S. Cl. ......................... 435/69.4; 435/325; 435/360; 435/320.1; 530/399; 514/2; 514/12
[58] Field of Search ................................. 514/2, 12, 21; 435/69.4, 320.1, 325, 358; 536/235, 24.1; 530/399

[56] References Cited

U.S. PATENT DOCUMENTS

| | | |
|---|---|---|
| 5,035,887 | 7/1991 | Antoniades et al. . |
| 5,149,691 | 9/1992 | Rutherford . |
| 5,165,938 | 11/1992 | Knighton . |
| 5,334,532 | 8/1994 | Tackney et al. . |
| 5,358,856 | 10/1994 | Baltimore et al. . |
| 5,428,135 | 6/1995 | Lyons et al. . |

FOREIGN PATENT DOCUMENTS

| | | |
|---|---|---|
| 0 259 632 | 3/1988 | European Pat. Off. . |
| 3 834 079 | 4/1990 | Germany . |
| 90/01550 | 2/1990 | WIPO . |
| 90/08163 | 9/1990 | WIPO . |
| 90/03143 | 2/1993 | WIPO . |

OTHER PUBLICATIONS

Ostman et al., J. Biol. Chem. 263, pp. 16202–16208, 1988.
Eichner et al., Eur J. Biochem. 185, pp. 135–140, 1989.
Jackson et al., TIBS, 15:477–483, 1990.
Schneppe et al., Gene 143, pp. 201–209, 1994.
Hannink et al., "Deletions in the C–Terminal Coding Region of the v–sis Gene: Dimerization IS Required for Transformation", Molecular andCellular Biology 6(4):1304–1314 (1986).
King et al., "In vitro mutagenesis of the v–sis transforming gene defines functional domains of its growth factor–rel product", Proc. Natl. Acad. Sci. USA 82:5295–5299 (1985).
Sauer et al., "Deletions in the N–Terminal Coding Region of the v–sis Gene: Determination of the Minimal Transfo Region", Journal of Virology 59(2):292–300 (1986).
Haller et al., "Linker Scanning Mutagenesis of the Internal Ribosome Entry Site of Poliovirus RNA", Journal of V 66(8):5075–5086 (1992).
Betsholtz et al., "cDNA sequence and chromosomal localization of human platelet–derived growth factor A–chai its expression in tumour cell lines", Nature 320(6064):695–699 (1986).

*Primary Examiner*—John Ulm
*Assistant Examiner*—Christine Saoud
*Attorney, Agent, or Firm*—Nixon & Vanderhye, P.C.

[57] ABSTRACT

The recombinant production of PDGF-AB in mammalian cells is disclosed by means of a bicistronic vector system in which an IRES sequence is located between the first and second cistrons and in which the B chain coding gene is located in the first cistron. The disclosed expression unit allows the equilmolar expression of the A and B polypeptide chains.

8 Claims, 13 Drawing Sheets

Analysis of purified PDGF by SDS-PAGE

PROCESS FOR PRODUCING A PHARMACEUTICAL PREPARATION OF PDGF-AB

This is a continuation of application Ser. No. 08/387,845, filed Apr. 24, 1995, now U.S. Pat. No. 5,665,567, which is the National Stage entry of PCT/EP93/02295 filed Aug. 26, 1993.

The invention relates to the recombinant preparation of PDGF-AB (rPDGF-AB), in mammalian cells as host cells, which is essentially free of the homodimeric contaminating products PDGF-AA and PDGF-BB.

It has been possible for many years to prepare individual proteins, whose genes were isolated by cloning, in different prokaryotic and eukaryotic cells, following manipulation and gene transfer. Correct folding and processing, and, where appropriate, post-translational modification as well, which are often not carried out correctly in prokaryotic and lower eukaryotic expression systems, are necessary for achieving the complete biological activity of many proteins. For this reason, mammalian cells are frequently used as hosts. In addition to this, mammalian cells are able to secrete large quantities of proteins.

For various reasons, the simultaneous preparation of two or more protein chains is often required. For example, many natural proteins are, in their functional form, composed of several subunits (e.g. antibodies). In nature, the association of the different subunits of complex proteins takes place after protein synthesis. Other components of the cellular apparatus frequently participate in this association as catalysts or controlling elements, with folding of the original structures taking place on occasion. Disturbances of the association, e.g. by an equal synthesis of the individual components, can have negative consequences both for the proteins which are to be formed and for the host cell. In nature, this system is subject to sophisticated regulation, which is for the most part cell-specific. Since this regulation is in general not adjustable in genetically manipulated cells, the alternatives explained below were developed and used for the simultaneous preparation of several foreign proteins:

1) The genes are integrated separately into expression vectors and then cotransferred in an appropriate ratio into the cells. This presupposes that several plasmid copies are taken up at the same time in a stable manner and continue to be harboured during division. The ratio of the expression of the different genes to each other depends both on the copy number and on the site of integration in the genome of the host cell. It is possible, by elaborate screening processes, to isolate cell clones which express the individual gene products in the desired ratio.

2) In order to level out the copy number, the different genes are placed in independent transcription units on one vector. While this, to a large extent, ensures stoichiometric representation of the genes, this process is also subject to problems. Thus, even if expression units having promoters of equal strength are used, it is in no way guaranteed that the mRNAs, which encode the different proteins, have the same stability and translation efficiency. Nor does the transcriptional efficiency of the two genes necessarily need to be identical. In this case, the stoichiometry of expression is produced stepwise using recombinant DNA stratagems (positioning of the transcription units with respect to each other and modulation of the strength of the individual promoters by removing or adding individual elements).

3) Bicistronic or multicistronic vectors were developed in order to avoid the problems connected with the stability of the mRNA of different transcripts. For this purpose, the individual reading frames of the gene segments—cistrons—encoding the protein chains lie on one transcription unit (expression unit). Expression of the multicistronic gene is effected using a single promoter. While the first cistron in such vectors is normally translated very efficiently, translation of the subsequent cistrons depends on the intercistronic sequences. If normal 5' untranslated sequences (5'UTR) from monocistronic genes are used for these intercistronic sequences, expression of the subsequent cistron is usually very low (as a rule, about 0.5 to 2% of the translation of the first cistron, Kaufman et al., 1987; Boel et al., 1987). It was initially possible to increase this efficiency to about 20% by inserting leader sequences (high efficiency leaders, HEL). It was subsequently possible, with the discovery and use of particular cellular and viral sequences which render possible internal initiation of translation (IRES; Jackson et al., 1990), to achieve a translation ratio between the first and subsequent cistron of 3:1.

Translation plays the key role in the use of bicistronic or multicistronic vectors. Normally, translation is initiated in eukaryotes in accordance with the "cap"-dependent mechanism, in the course of which a preinitiation complex, consisting of proteins and RNA, is constructed at the 5' end of an mRNA possessing a "cap" (methylated nucleotide). From this point, a suitable translation initiation codon is sought out, starting from which the translation is begun. It is believed that this takes place by way of a "scanning" process in which the preinitiation complex moves along the mRNA in the 3' direction. Apart from a few exceptions, the cistron lying at the 5' end is always efficiently translated in this manner (Kozak, 1989). All the subsequent cistrons are either not translated at all or only translated very inefficiently. It was possible to improve the translational efficiency of the subsequent cistrons (e.g. Falcone and Andrews, 1991 and references therein) by optimizing the distance between the genes (intercistronic regions; Kozak, 1987; Wirth et al., 1991) or by using so-called "high efficiency leader" sequences (HEL, see above). HEL's are those 5' untranslated regions of genes or of other sequences which stimulate initiation of "cap"-dependent translation. However, even in constructs of this nature, the expression values which can be achieved for the second and subsequent cistrons are always clearly lower than those of the first cistron regulated in a "cap"-dependent manner.

A mechanism for initiation translation internally, discovered in recent years, makes use of specific nucleic acid sequences. These sequences include the untranslated regions of individual picorna viruses, e.g. poliovirus and encephalomyocarditis virus, (Pelletier and Sonenberg, 1988; Jang et al., 1988; Jang et al., 1989) as well as some cellular proteins, e.g. BiP (Macejak and Sarnow, 1991). In the picorna viruses, a short segment of the 5' untranslated region, the so-called IRES internal ribosomal entry site), is responsible for the internal binding of a preinitiation complex. In addition to this, further segments from this region are necessary for efficiently initiating this translation. Thus, it is evident, for example, that not only the 400 base pairs upstream of the IRES, but also the extreme 5' part of the picorna virus untranslated region, are necessary for efficient translation (Simoes and Sarnow, 1991). On the other hand, the "capping", which is a prerequisite for the normal mechanism of initiation translation, leads to a reduction in the efficiency of internal initiation by poliovirus IRES, if it is localized at the 5' end of a corresponding mRNA (Hambridge and Sarnow, 1991). The negative effect is abolished if the IRES is responsible for initiating the second cistron, that is if a cistron is situated between the "cap" and the IRES.

IRES elements can thus function as initiators of the efficient translation of reading frames. In doing this, they have no influence on the "cap"-dependent translation of the first cistron. Conversely, in addition, any effect on IRES-dependent initiation appears to be independent of "cap"-dependent translation initiation. The mechanisms of the two processes also clearly differ in the use of different cellular factors (Meerovitch et al., 1989; Jang and Wimmer, 1990). In the past, several investigations have been published in which bicistronic expression plasmids were used (Adam et al., 1991; Ghattas et al., 1991; Kaufman et al., 1991; Wood et al., 1991; Wirth et al., 1991). However, since "cap"-dependent translation is evidently stronger than IRES-dependent translation, it was not possible to achieve stoichiometric expression of two protein chains. Previous applications have therefore concentrated on using selective markers in the second cistron. The close coupling of the expression of the selective marker with that of the gene to be expressed, which constitutes the first cistron, is particularly advantageous when selecting for a high level of expression, in particular if prior gene amplification is required.

However, the synthesis of equimolar quantities of protein by bicistronic or multicistronic expression vectors has not previously been achieved. The equimolar expression of two different protein chains is of particular importance for the recombinant preparation of the growth factor from blood platelets, "platelet-derived growth factor" (PDGF), one of the principal mitogens in human blood serum. PDGF purified from human blood platelets consists of two different, but closely related, polypeptide chains which are linked to each other by disulphide bridges. Under reducing conditions, the dimeric PDGF disassociates into its monomeric subunits, of which the larger ($M_r$ 15–17,000 D) has been designated the PDGF-A chain and the smaller ($M_r$ 14,000 D) the PDGF-B chain (Johnsson et al., 1984).

The PDGF-A and PDGF-B protein chains are encoded by different genes. It has been possible to elucidate the complete structure of both gene products by means of cDNA cloning (Ratner et al., 1985, Betsholtz et al., 1986). In this context, it emerged that both PDGF molecules are initially synthesized as unusually long precursor molecules and are subsequently processed intracellularly to give rise to the mature PDGF chains. Two different PDGF-A transcripts, which differ by the presence or absence of a 69-bp segment in the 3' region, can be accounted for on the basis of alternative splicing (Betsholtz et al., 1986; Wise et al., 1989). This insert gives rise to change in the coding segment, resulting in short (PDGF-$A_K$, 110 amino acids) and long (PDGF-$A_L$, 125 amino acids) variants of the PDGF-A chain being formed. Both variants are detectable as normal cellular proteins alongside each other, with the shorter form being the more frequently occurring species (Matoskova et al., 1989; Young et al., 1990).

The two genes are located on different chromosomes and demonstrate a high degree of homology. A large number of studies show that the two genes are subject to different regulatory mechanisms. A consequence of this is that, in nature, the two PDGF chains are produced in different cell types in different ratios to each other.

All the three possible isoforms of PDGF (AA, AB and BB) occur naturally and are stored in blood platelets in so-called α-granules. Apart from the PDGF-AB heterodimer, which forms the major quantity, up to about 30% PDGF-BB can also be isolated from aged human blood platelets (Hammacher et al., 1988). Freshly prepared blood platelets also contain a high proportion (27%) of PDGF-AA (Hart et al., 1990). It can, therefore, be assumed that in the precursor cells of the thrombocytes, i.e. the megakaryocytes, the proportion of the two homodimers together corresponds approximately to that of the AB heterodimer. Since the concentration of each PDGF species in the blood platelet should correlate directly with its individual importance in the wound-healing process, the most frequent isoform, i.e. PDGF-AB, in particular, receives special emphasis in the search for a "wound-healing hormone".

Each of the different isoforms possesses biological activity in-vitro. It was only the availability of highly purified, recombinant PDGF isoforms (Hoppe et al., 1989; Hoppe et al., 1990) which made possible comparative studies aimed are differentiating the different spectra of activity of the various PDGF species. By now, a series of investigations confirms the different potency of PDGF-AA, PDGF-AB and PDGF-BB in chemotaxis and DNA-proliferation tests (Hosang et al., 1989; Nister et al., 1988; Reilly & Broski, 1989; Siegbahn et al., 1990), as well as their differing influence on the liberation of inositol 1,4,5-triphosphate, production of diacylglycerol and $[Ca^{2+}]_i$ mobilization (Block et al., 1989; Sachinidis et al., 1990 A, 1990 B). Two different PDGF receptor populations, of which the PDGF α-receptor binds all the PDGF isoforms and the β-receptor binds only PDGF-BB (Hart et al., 1988; Heldin et al., 1988) provide a plausible explanation for how differences in the effect of the PDGF isoforms can evolve by way of their differential receptor-activating ability. The measurable, and different, in-vitro effects of the PDGF isoforms, together with the demonstration of two different receptor populations, permit the conclusion that the in-vivo spectra of activity of PDGF-AA, PDGF-AB and PDGF-BB are different. For this reason, the production of pure PDGF-AB, without the presence of PDGF-BB or PDGF-AA as a contaminating protein, is desirable. In order to obtain a homogeneous, well-characterized heterodimer, the homodimers would otherwise have to be completely eliminated by purification, which is additionally exacerbated by the very similar chromatographic properties of all the PDGF species.

A series of different routes for preparing recombinant PDGF homodimers, in particular PDGF-BB, has been known in part for a relatively long time (Kelly et al., 1985; Heldin et al., 1986; Hoppe et al., 1989; Beckmann et al., 1988; Bywater et al., 1988; Stroobant & Waterfield 1984). A process for preparing highly pure PDGF-AB was described by Hoppe et al. (1990, see also PCT/EP 90/00 063). In this process, the inactive monomers, prepared separately in different *E. coli* cells, are converted into biologically active PDGF-AB by renaturation in-vitro.

Despite varying length of the A and B single strands, the gene products of the three PDGF isoforms that have been synthesized hitherto exhibit biological activities which to a large extent correspond with each other.

The criteria for the simultaneous expression of two (or more) proteins, which were mentioned in the introduction, apply to the heterologous expression of PDGF-AB heterodimers in eukaryotic systems. The previously published strategies for preparing PDGF-AB in recombinant CHO cells (Östman et al., 1988) and using yeast expression systems [EP 0 259 632] correspond to the case example discussed under 2) above, where both PDGF genes are located on one vector in independent transcription units. Quantification of the different PDGF dimers expressed in this manner in CHO cells gave 19% for PDGF-AA, 69% for PDGF-AB and 12% for PDGF-BB (Östman et al., 1988).

Not only the stoichiometric representation of both genes, but also, as a first priority, their coordinated expression, are therefore to be viewed as fundamental prerequisites for the preferred synthesis of PDGF-AB heterodimers using eukaryotic expression systems. For this reason, bicistronic expression units present themselves as possible aids for expressing heterodimeric proteins and thus PDGF-AB. A system of this nature is also described for the expression of PDGF in WO 90/01550. However, as explained in more detail under 3) above, these constructs yield only very limited expression rates for the second (and subsequent) cistron. Depending on the PDGF chain located in the first cistron, homodimers of this type are predominantly formed. Attempts which have previously been described in the literature to express both PDGF genes in a eukaryotic cell using other expression systems led to proportions of homodimer byproduct in the region of 30% or more. In order, nevertheless, to obtain PDGF-AB using these cell systems, elaborate and extremely wasteful purification techniques must be employed.

The object of the invention is, therefore, to create an expression system using PDGF-AB which can be prepared without any appreciable contamination by the respective homopolymers.

In accordance with the invention, it was possible to achieve the object by using a construct which, while, in a manner known per se, making use of the IRES sequence between the first and second cistron, introduces the gene encoding PDGF-B into the first cistron. Surprisingly, it has been found, according to the invention, that, after transfection with these constructs, the host cells secrete PDGF-AB containing negligible quantities of homodimers. The yield and profitability of the subsequent protein purification processes are thereby considerably improved.

Accordingly, the invention relates to a bicistronic expression unit for the recombinant preparation of heterodimeric PDGF-AB in mammalian cells as host cells, which unit is characterized by the general formula $$p\text{-}5'UTR\text{-}C_1\text{-}IRES\text{-}C_2\text{-}3'UTR\text{-}polyA,$$

in which p is a transcriptional promoter,

5'UTR is an untranslated nucleotide sequence, $C_1$ is a cistron which contains a gene encoding the B chain of PDGF, a biologically active analog, or a fragment thereof, IRES is a nucleotide sequence of viral, cellular or synthetic origin, which sequence is responsible, at the stage of translation, for internal initiation, $C_2$ is a cistron which contains a gene encoding the A chain of PDGF or a biologically active analog, or a fragment thereof, 3'UTR is an untranslated nucleotide sequence, and polyA is a polyadenylation signal, where $C_1$, IRES and $C_2$ are connected to each other in an operative manner.

All those promoters which are effective in eukaryotic cells, i.e. which can initiate gene expression in eukaryotic cells, are suitable as promoters. In particular, all constitutive and inducible promoters of viral (for example the "long terminal repeats", LTR's, of retroviruses, or the herpes simplex thymidine kinase promoter), cellular (for example the interferon or the ubiquitin promoter) or synthetic origin can be used. The SV40 promoter is preferred according to the invention.

The 5'UTR and the 3'UTR are any, as a rule untranslated, nucleotide sequences which can contain regulatory elements. According to the invention, the sequences from SV40 according to Artelt et al. (1988) are suitable, for example.

The first cistron, $C_1$, can contain the complete PDGF-B precursor sequence (SEQ ID NO: 3), its analogs and any fragment which encodes a biologically active PDGF-B chain. In particular, the v-sis gene (product of simian sarcoma virus (SSV)), which is homologous to the PDGF-B chain, and the base pairs 283 to 609 according to SEQ ID NO: 3, which encode the mature PDGF-B chain, are suitable in this connection.

In an analogous manner, the second cistron, $C_2$, can contain the long or short PDGF-A precursor sequence (PDGF-$A_L$ or PDGF-$A_K$—SEQ ID NO: 1) as well as any fragments which encode a biologically active PDGF-A chain. In particular, the fragment according to base pairs 353 to 682 according to SEQ ID NO: 1, which encodes the mature PDGF-A chain, is suitable.

All those sequences of viral, cellular or synthetic origin which mediate an internal binding of the ribosomes can be used as an IRES. Examples of such sequences are the IRES from poliovirus Type 1 according to SEQ ID NO: 5, which encompasses the first 628 nucleotides of the 5' untranslated region of poliovirus Type 1, and, additionally, the 5'UTR of encephalomyocarditis virus (EMV), of "Theiler's murine encephalomyelitis virus" (TMEV), of "foot and mouth disease virus" (FMDV), of "bovine enterovirus" (BEV), of "coxsackie B virus" (CEV), or of "human rhinovirus" (ERV), or the "human immunoglobulin heavy chain binding protein" (BIP) 5'UTR, the Drosophila antennapediae 5'UTR or the Drosophila ultrabithorax 5'UTR, or genetic hybrids or fragments from the abovelisted sequences. The IRES from poliovirus Type 1 according to SEQ ID NO: 5 is preferred according to the invention.

The invention further relates to recombinant DNA vectors which contain the expression unit according to the invention. A vector which is preferred according to the invention is depicted in FIG. 4B, as is its preparation in FIGS. 1 to 3.

In addition, the invention includes host cells which are mammalian cells and which are transformed with a vector which carries the expression unit according to the invention. Preferably, the cells are CHO or BEK cells, the latter being particularly preferred. A BEK cell which was transformed according to the invention was deposited with the Deutsche Sammlung von Mikroorganismen und Zellkulturen GmbH (DSM) (German collection of microorganisms and cell cultures) on Aug. 11, 1992 under the designation 91-21-4D. The deposition number DSM ACC2045 was allocated to it.

In addition to this, the invention includes processes for preparing heterodimeric rPDGF-AB, in the course of which processes mammalian cells, as host cells which harbour the expression unit according to the invention inserted in an operative manner, are cultivated in a suitable medium and the resulting rPDGF-AB is separated off from the cells and the medium. All known media for cultivating mammalian cells, including synthetic, protein-free or protein-poor production media, are suitable as the medium. DBEM (Dulbecco's modified Eagle medium), enriched with 4.5 g/l glucose and 5 to 10% FCS, was preferred according to the invention.

The rPDGF-AB is separated from the cells and the medium by conventional processes (cf., for example, Östman et al. 1988). A highly efficient process, which was developed for PDGF-AA (Eichner et al., 1989), is preferably used according to the invention.

The invention finally relates to heterodimeric rPDGF-AB which is essentially free of homodimeric contaminating products and which can be obtained by cultivating the above-described host cells according to the invention. Surprisingly, it has emerged that the host cells which are transformed with the construct according to the invention secrete the heterodimeric PDGF-AB at a purity of 90% or more, based on the total quantity of PDGF formed. According to the invention, PDGF-AB is preferred which is made available by cultivating BHK cells which have been transformed with the construct according to the invention, for example those cells which were deposited with the German collection of microorganisms and cell cultures (DSM) on Aug. 11, 1992 under the designation 91-21-4D (deposition number DSM ACC2045).

The rPDGF-AB according to the invention primarily differs from the previously known recombinant PDGF-AB products on account of its high degree of purity. As remarked in the introduction, no recombinant process has hitherto been described in which 90% or more of the resulting product consists of the heterodimer. Since complete separation of the homodimers from the heterodimer is virtually impossible, the known products are inevitably mixtures of all 3 isoforms.

In addition to this, the known products, depending on their preparation, suffer from disadvantages in many respects. For example, it is known that heterologous gene expression in yeast cells, as described in EP 259 632 or 288 307, leads to protein products whose glycosylation patterns are altered as compared with the human product. Furthermore, PDGF-B expressed in yeast cells is, at least in part, incompletely processed and/or is proteolytically degraded (cf. WO 92/01716). Products of this nature thus have an altered carbohydrate pattern and are contaminated with products of proteolytic degradation. To avoid the aforesaid disadvantages, WO 92/01716 describes processes for preparing modified PDGF chains in which the consensus sequences for glycosylation, and the protease-sensitive domains, have been removed. However, modifications of this nature affect the biological activity of the product (cf. WO 92/01716).

According to a particularly preferred embodiment of the invention, heterodimeric rPDGF-AB is obtained by cultivating BEK cells which have been transformed according to the invention, and in particular by cultivating the host cells 91-21-4D having the deposition No.: DSM ACC2045.

In addition, WO 90/08163 discloses the recombinant preparation of PDGF-AB in bacterial cells, in particular in E. coli, which preparation inevitably leads to an unglycosylated product. However, a PDGF-B chain expressed by this process in E. coli cells is truncated at the amino terminus by 12 amino acids. In addition to this, the product from bacteria must be renatured in-vitro, a procedure in which the correct intermolecular and intramolecular formation of the disulphide bridges, and the correct folding of the protein, is not guaranteed, with the consequence that the immunological properties of the product may be altered and the biological activity affected.

The heterodimeric rPDGF-AB according to the invention is preferably formulated with pharmaceutically tolerated auxiliary agents and excipients as a pharmaceutical preparation, in particular for wound healing. In this connection, it can be contained as the active compound in plasters and wound bandages and the like. While it is particularly suitable for topical application, other forms of administration, in the course of which the active compound is introduced into the wound or administered subcutaneously, are also suitable. For example, the PDGF-AB can be administered subcutaneously, in a suitable matrix having a depot function, in the peripheral region of the wound, or directly injected subcutaneously.

Further, the rPDGF-AB of the present invention is suitable for manufacturing cosmetical preparations, for example for skin regeneration, skin smoothening, prevention of scarring or of skin ageing as well as for application on sunburn.

Suitable auxiliary agents and excipients include water-based cellulose gels, biodegradable polymers and any ointment basis and cream basis, and sprays. Furthermore, additional active compounds which affect wound healing, such as, for example, collagen, fibronectin, factor XIII, fibroblast growth factor (aFGF and bFGF), transforming growth factor type α or β, epidermal growth factor, insulin or "insulin-like growth factor" (IGF I and II), or further growth factors, may be contained in the preparations according to the invention. The products according to the invention can, for example, also be present in wound bandages in aqueous solution.

The invention is explained below with the aid of examples:

AB: from human blood platelets, from PROMEGA Corp. No. G 5161;

BB: recombinant from yeast, from PROMEGA Corp. No. G 5191;

AA: recombinant from BHK cells, about 70% pure (Eichner et al., 1989).

Using PDGF'S from eukaryotic sources, this assay gives a specific signal with PDGF-AB (from human blood platelets), accompanied by a slight cross reaction with PDGF-BB.

Figure 6:
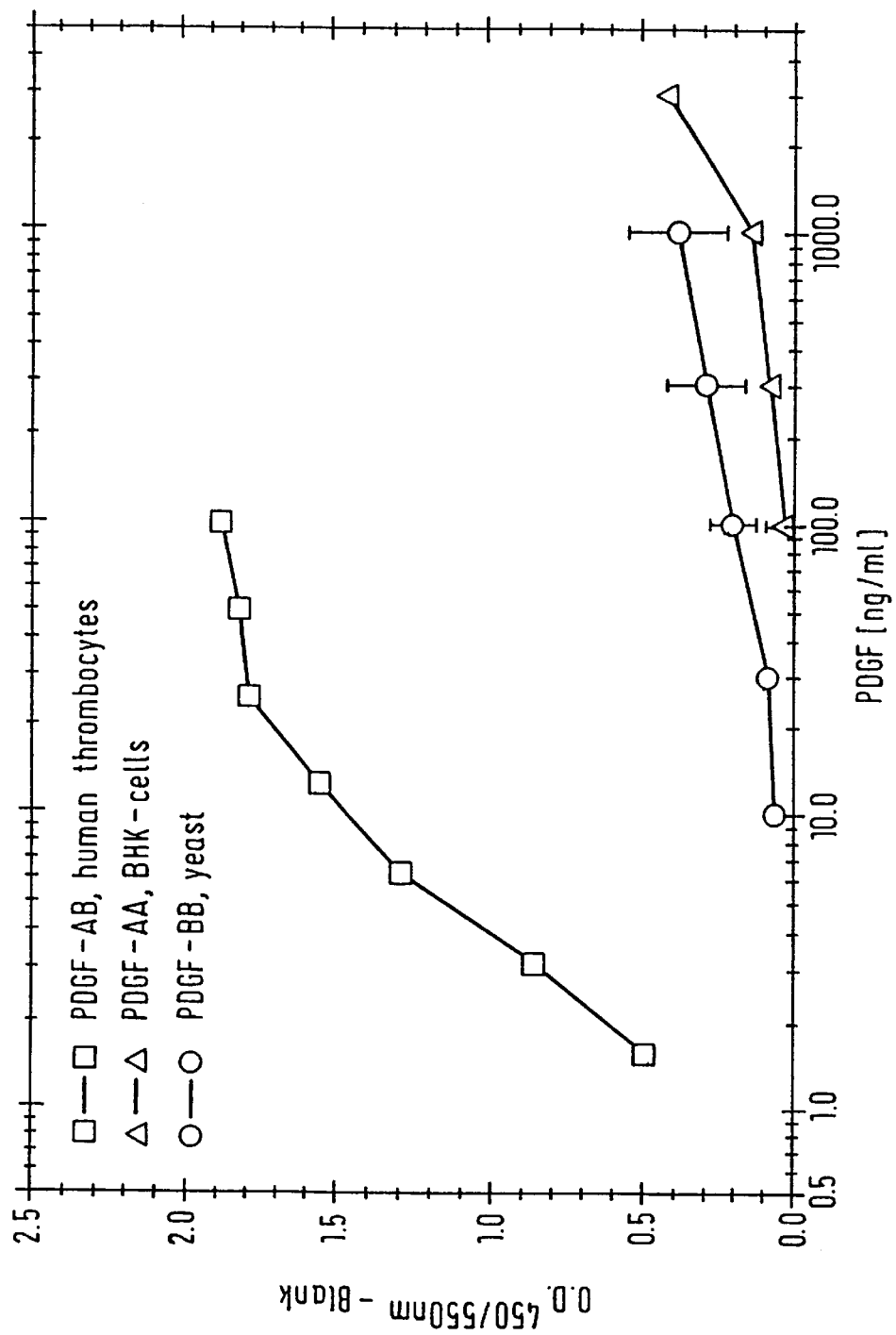
FIG. 6) Sandwich ELISA for detecting PDGF-AB using a monoclonal and a polyclonal anti-PDGF antibody: calibration curves from PDGF standards. Polystyrene plates were coated with sheep anti-mouse IgG and subsequently incubated with a mouse hybridoma supernatant (from clone 1B3, contains monoclonal antibodies against the B chain in PDGF-AB and PDGF-BB); following incubation with various PDGF standards, the bound PDGF was detected using a polyclonal rabbit anti-PDGF-AA, followed by peroxidase-labelled anti-rabbit IgG; source of the PDGF standards.
Figure 7:
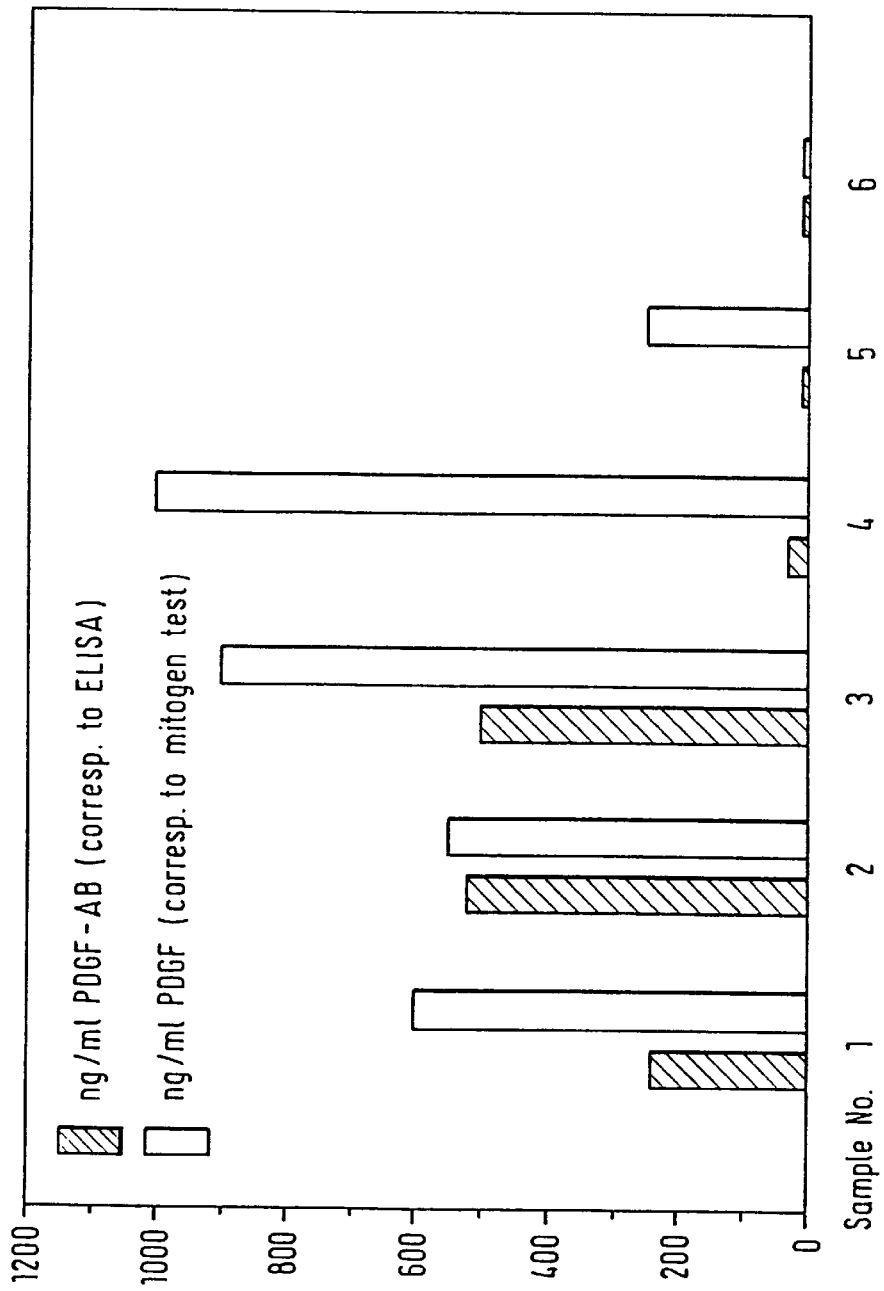

FIG. 7) Detection of PDGF-AB in culture supernatants of recombinant BHK cells using PDGF-AB-ELISA: (calibration curves from standards, see FIG. 6). The depicted samples derived from BHK cells which had been transfected with the following vector constructs:

Sample: No. 1: pSBC-A/B,
No. 2: pSBC-B/A
No. 3: pSBC-2-PDGF-A+pSBC-2-PDGF-B,
No. 4: pSBC-2-PDGF-A,
No. 5: pSBC-2-PDGF-B,
No. 6: pSBC-2-control FIG. 8) Analysis of purified rPDGF on SDS PAGE. The samples were separated on a 13.5% polyacrylamide gel in the presence of SDS and subsequently stained with Coomassie blue.

```
5' polio #1  5'TTT CTGCAG AAGCTT AAAACAGCTCTGGGG3'     (SEQ ID NO: 13)
                 pstI  HindIII 3' polio #2  5'TT GCGGCCGC AATCCAATTCGCTTTATG3'        (SEQ ID NO: 14)
                 NotI
```

1, 6, 11=molecular weight markers (PHARMACIA) [14400, 20100, 30000, 43000, 67000, 94000 D]
2=pSBC-B/A
3=pSBC-2-PDGF-A+pSBC-2-PDGF-B
4=pSBC-A/B
5=pSBC-2-PDGF-A
7–10=same application sequence as in 2–5, with the addition of 10% (v/v) β-mercaptoethanol (10 min, 95° C.) in each case The analysis of the purified secretory products on SDS-PAGE correlates with the result from the analysis of the culture supernatants (Tab. 2). It can clearly be seen, in particular from the bands of the PDGF monomers arising under reducing conditions, that transfection cell pools of the pSBC-2PDGF-A+pSBC-2-PDGF-B (cotransfer) and pSBC-A/B (PDGF-A chain in the first cistron) group predominantly secrete PDGF-AA homodimers.

The PDGF which can be isolated from pSBC-B/A culture supernatants bands at a molecular weight which is only to a trivial extent lower than that of the PDGF-AA which is applied as a reference. Under reducing conditions, both monomers can be detected in approximately equal amounts. The upper bands correspond to the monomer bands of the PDGF-A chain. It has already been shown for recombinant PDGF-AA from BHK cells that this material consists, in approximately equal proportions, of the complete PDGF-A chain and a C-terminally truncated species (Eichner et al., 1989).

The monomeric PDGF-A chains band at a $M_r$ of about 17 KD. The PDGF-B chain, which likewise occurs in a truncated form in the material isolated from pSBC-B/A supernatants, bands below this ($M_r$ 16 KD). The subspecies of the two chains were analyzed together by protein sequence analysis and unambiguously identified as PDGF-A and PDGF-B. Molecular weight differences in PDGF-B are, therefore, just as in the case of PDGF-A, possibly to be attributed to C-terminal truncations or altered glycosylation patterns. Accordingly, PDGF from pSBC-B/A supernatants consists of PDGF-A and PDGF-B chains in approximately equal amounts.

The PDGF-AA which was applied as a reference and which was likewise expressed in BHK cells is not glycosylated (Eichner et al., 1989), whereas PDGF expressed in CHO cells contains a carbohydrate proportion of about 7% (Kolvenbach et al., 1991). The PDGF-A monomers from both the PDGF-AA homodimer and the AB heterodimer agree well with each other in regard to their migratory behaviour on SDS-PAGE.

Figure 1A:
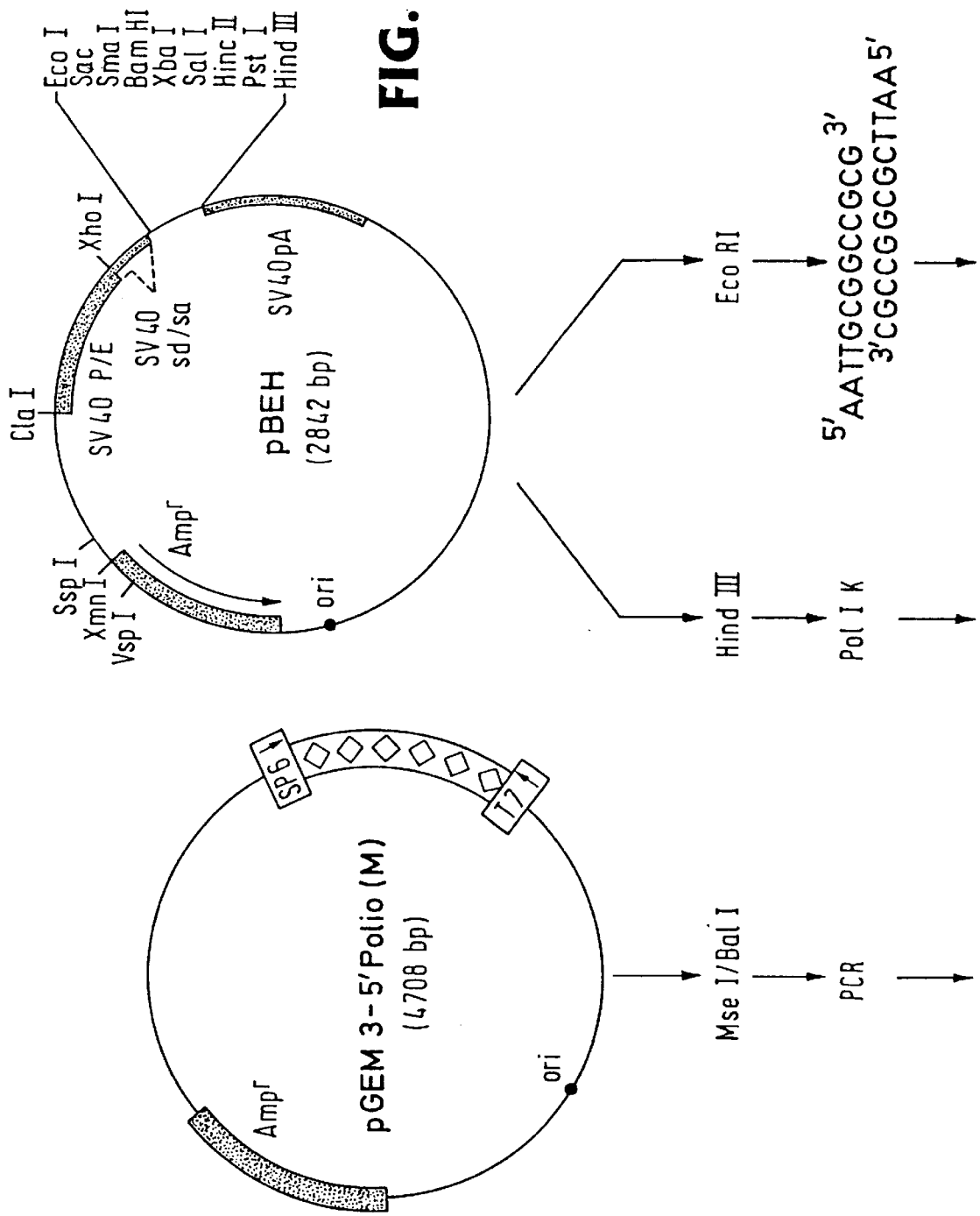
FIGS. 1A and 1B) Schematic representation of the preparation of the basic vectors pSBC-1 and pSBC-2.
Figure 1B:
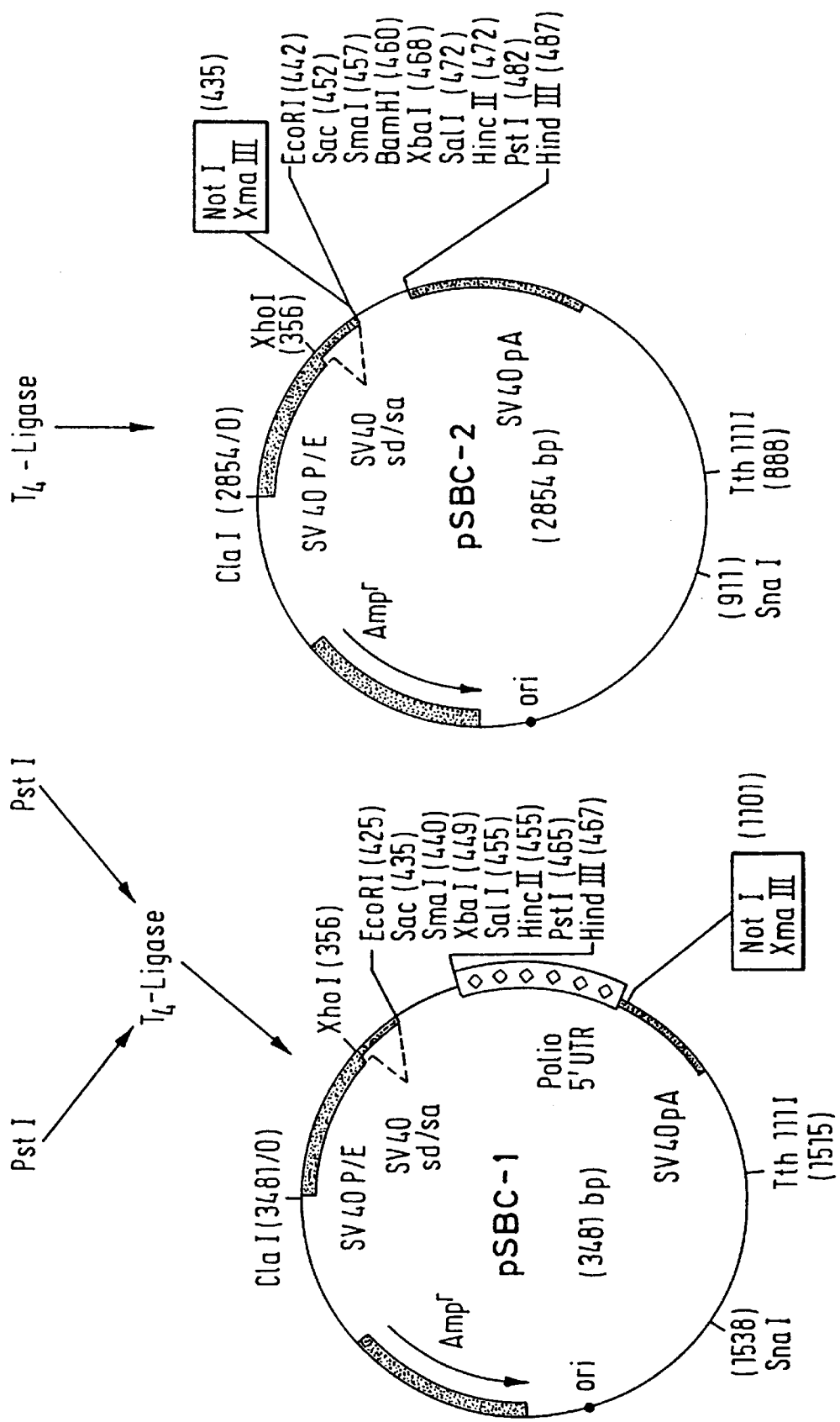

2. Expression of PDGF-AB Heterodimer Using the Bicistronic Vector System 2.1 Preparation of the Basic Vectors pSBC-1 and pSBC-2 (FIG. 1)

For constructing the vector pSBC-1, a 627 bp MseI/BalI fragment from the plasmid pGEM3-5' polio (M) (Sarnow, 1989) was used as the template for a PCR employing the following primers:

The 652 bp fragment attained after the amplification was treated with pol I K and then cleaved with PstI and inserted into the vector pBEH (Artelt et al., 1988), which had been prepared in a corresponding manner.

For constructing the vector pSBC-2, plasmid pBEH was linearized with Eco RI and the following oligonucleotide sequences were hybridized and inserted:

```
E-N-E #1  5'AATT GCGGCCGCG3'     (SEQ ID NO: 15)

E-N-E #2  3'CGCCGGCG CTTAA5'     (SEQ ID NO: 16)
```

2.2 Reconstitution of the Complete PDGF-3 Precursor Sequence

The plasmid pMVW-2 contains the cDNA of the human PDGF-B gene, which is incomplete in the 5'-translated region of the precursor sequence (Weich et al., 1986). In order to reconstitute the authentic PDGF-B precursor, a BclI cleavage site was introduced into the 5'-terminal region of the precursor by means of a C-T exchange in position 30 of the coding segment of clone pMVW-2. In the end, only a short segment of the coding region is lost as a consequence of this step and the locally encoded amino acid (aspartic acid) is preserved. Since, in most E. coli strains, the BclI cleavage site is resistant to enzymic cleavage as a result of methylation, the fragment containing this cleavage site must either be recloned into a dam⁻ strain or else amplified in a PCR step. The missing region of the precursor is then inserted as a synthetic SalI/BclI fragment [oligomers PPDGFB1 and PPDGFB2 (SEQ ID NO: 11+12)].

Figure 2:
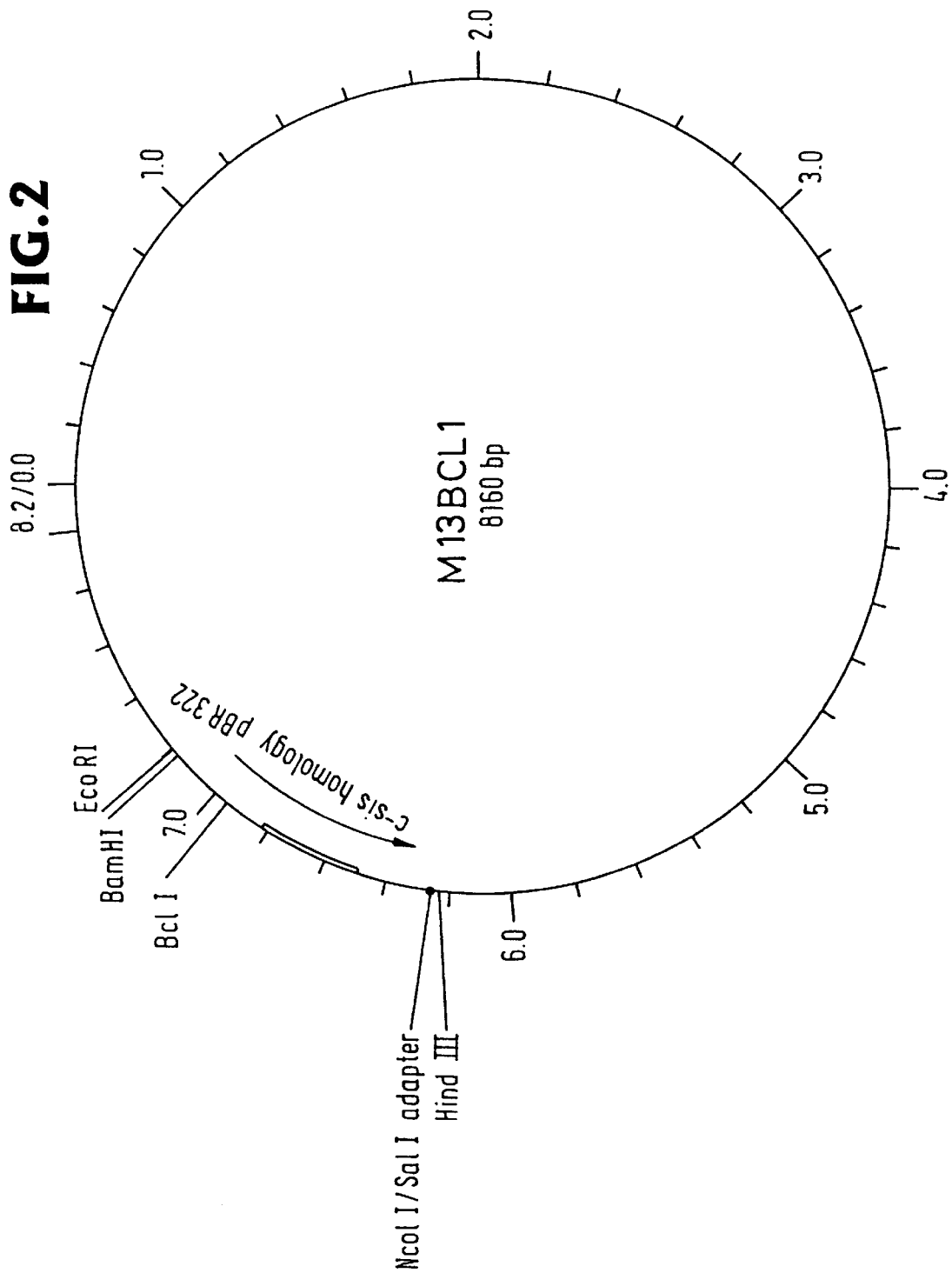
FIG. 2) Vector M13BCL1; the region from pMVW-2 which is homologous to c-sis (PDGF-B) is indicated on the vector map. The regions of the mature PDGF-3 and the NcoI/SalI (SEQ ID NO: 8+9) adapter are emphasized by black bars.

For this purpose, the 914 bp BamHI/NcoI fragment from pMVW-2 was first inserted by way of a synthetic adapter [oligomers NCCLSA1 and NCCLSA2 (SEQ ID NO: 8+9)] into the BamHI/SalI-cleaved bacteriophage M13mp19 (Pharmacia). This construct provided the necessary single-stranded DNA for the subsequent in-vitro mutagenesis step, which was carried out using the oligomer-directed in-vitro mutagenesis system (version 2) from Amersham, based on the method of Eckstein et al. [Taylor J. W., Ott J. and Eckstein F. (1985) Nucl. Acids Res. 13, 8764–8785; Nakamaye K. and Eckstein F. (1986) Nucl. Acids Res. 14, 9679–9698; Sayers J. R., Schmidt W. and Eckstein F. (1988) Nucl. Acids Res. 16, 791–802]. Using the synthetic primer [PDGBBCL (SEQ ID NO: 10)], a base exchange (C to T) is achieved, following mutagenesis, in position 144 of the sequence depicted under SEQ ID NO: 3, and thereby a BClI cleavage site introduced in the 5' region of the PDGF-B precursor. This mutagenesis derivative was designated M13BCL1 (FIG. 2).

Figure 3A:
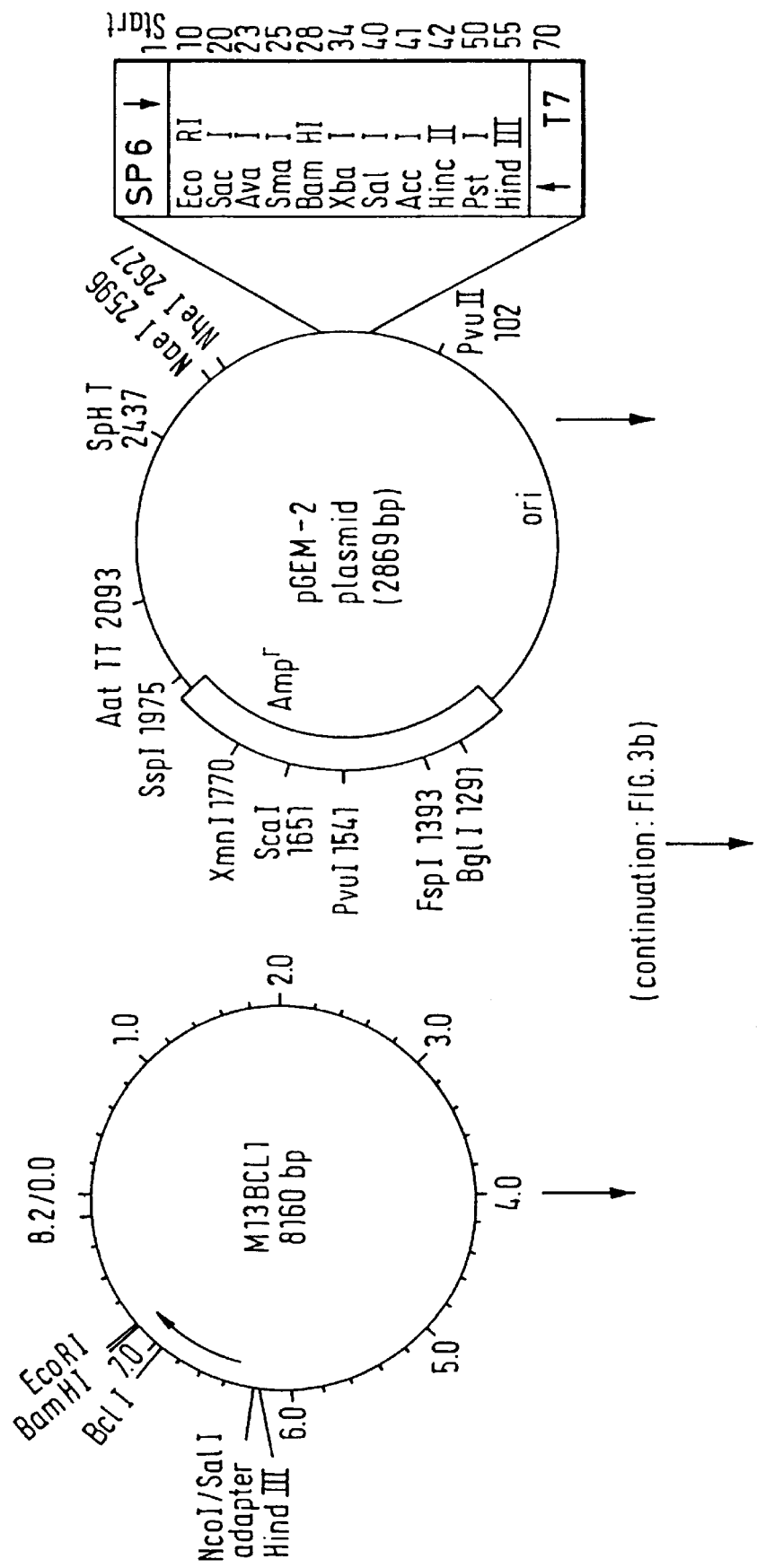
FIGS. 3A and 3B) Schematic representation of the reconstruction of the complete PDGF-B precursor sequence.
Figure 3B:
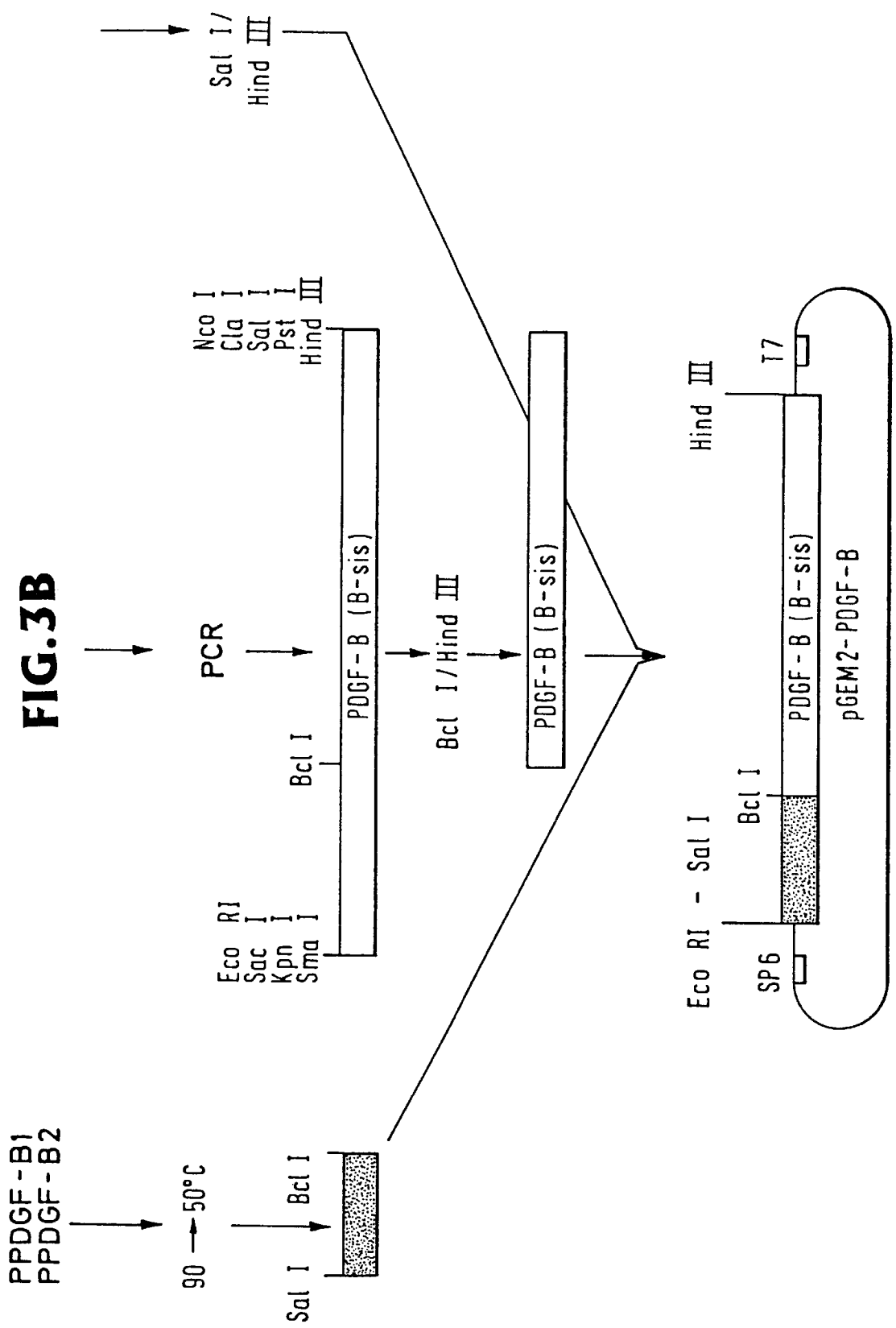

A 1100 bp fragment from M13BCL1 was amplified in a PCR step using the primers M1317MER and M-1324MER (SEQ ID NO: 6+7) and then subjected to a BclI/HindIII restriction; the resulting 770 bp fragment was isolated. The synthetic oligomers PPDGFB1 and PPDGFB2 (SEQ ID NO: 11+12) form the missing 5' region of the PDGF-B precursor up to the BclI cleavage site. After annealing, this double-stranded oligomer was then ligated, together with the 770 bp PDGF-B fragment, into the vector pGEM-2 (Promega), which had previously been prepared by being restricted with SalI/HindIII (FIG. 3). The authentic sequence of PDGF-B was verified by sequencing completely.

Figure 4A:
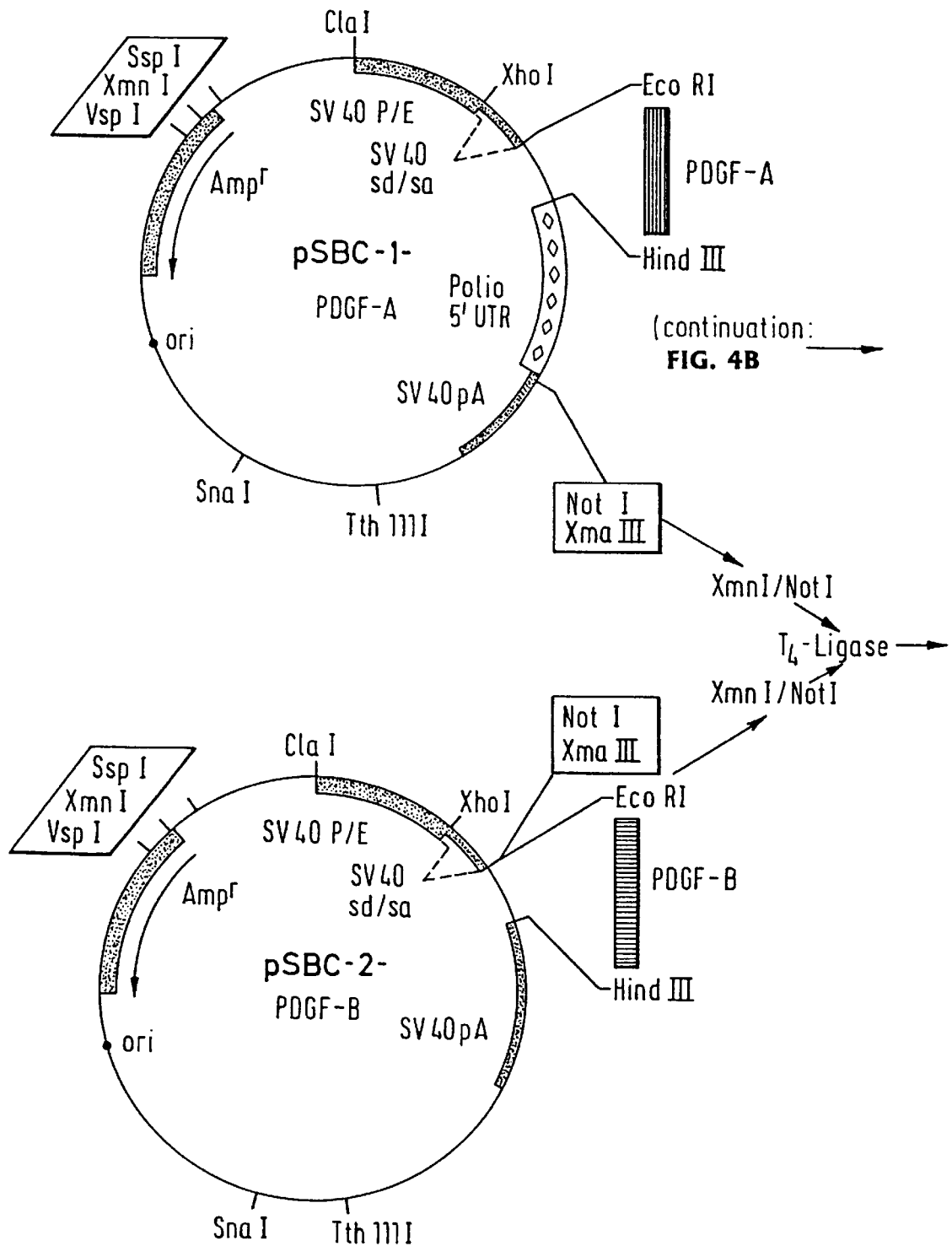
FIGS. 4A, 4B, 4C and 4D) Schematic representation of the construction of the bicistronic vector pSBC-A/B (FIGS. 4A and 4B), used for comparative purposes, and of the expression vector pSBC-PDGF-B/A according to the invention (FIGS. 4C and 4D) from the basic vectors pSBC-1 and pSBC-2. The expression vectors pSBC-PDGF-A/B and pSBC-PDGF-B/A differ from each other on the basis of the orientation of the coding cDNA sequences of the PDGF-A and PDGF-B chains, i.e. on the basis of their location on the plasmid as the first or second cistron, respectively, in the direction of reading.
Figure 4B:
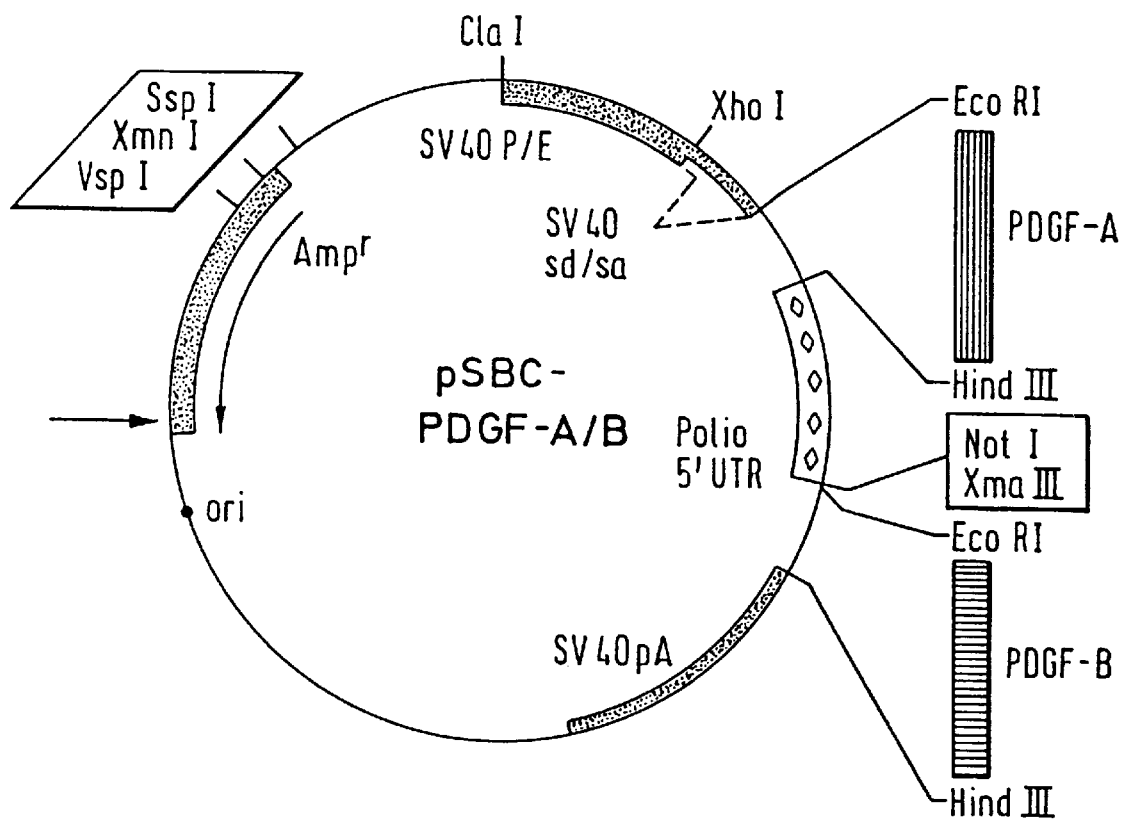
Figure 4C:
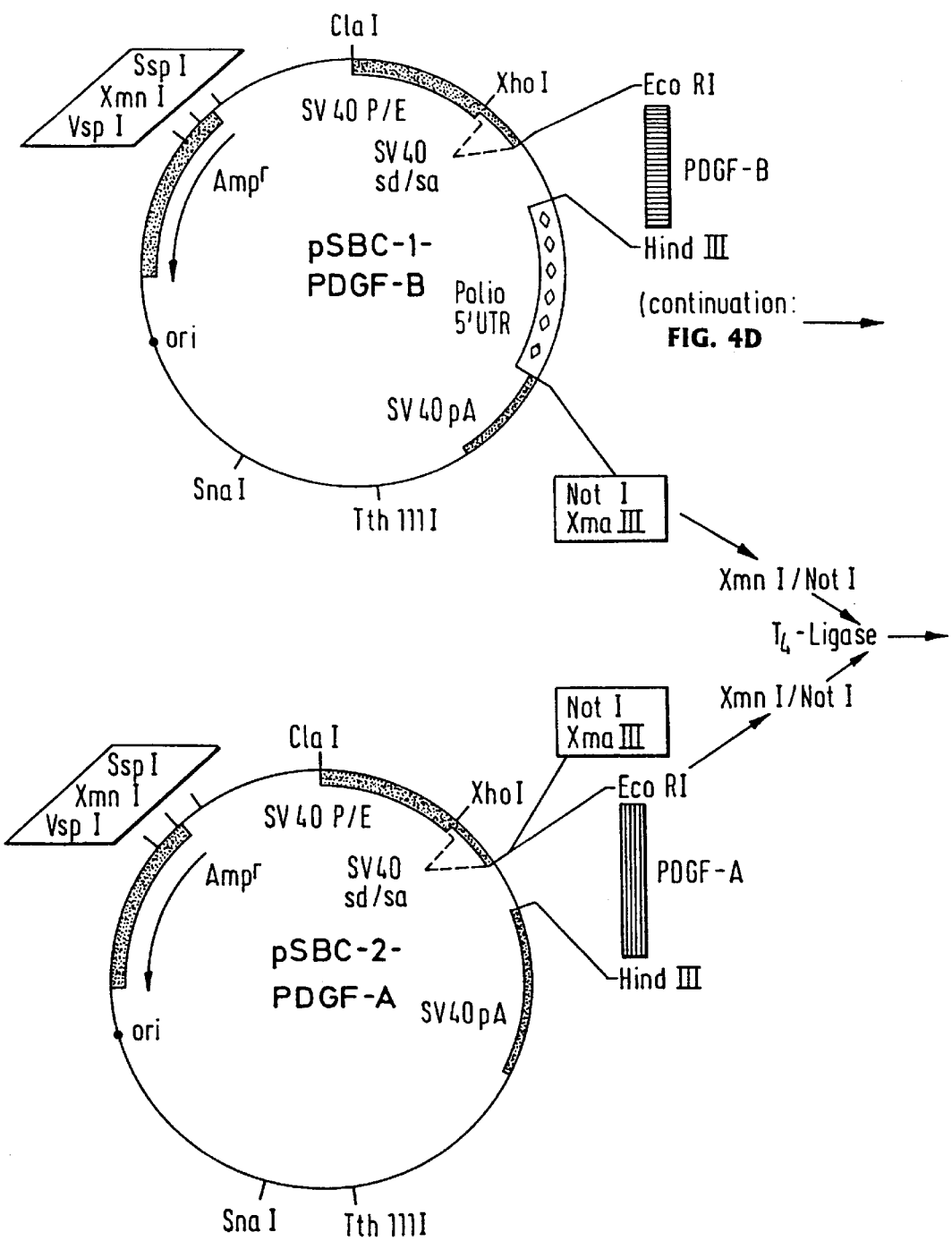
Figure 4D:
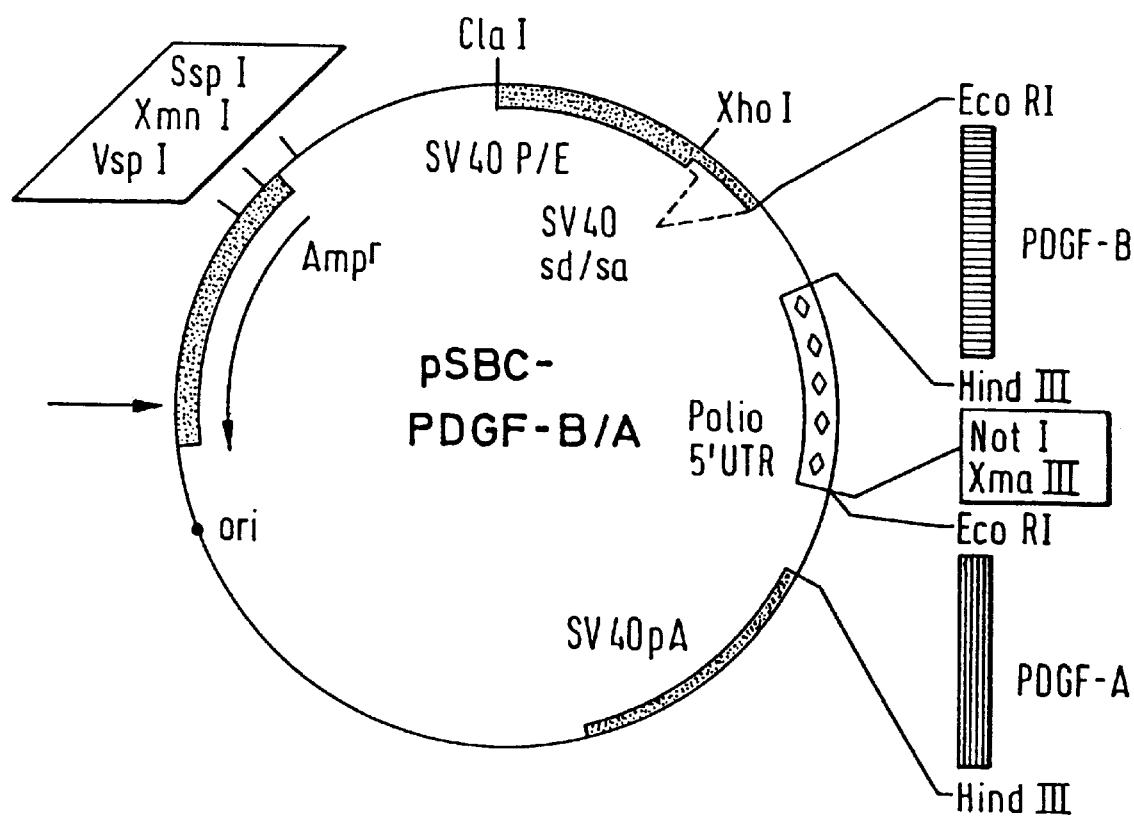

2.3 Construction of the Bicistronic Expression Vectors pSBC-PDGF-A/B and pSBC-PDGF-B/A for the PDGF-A and PDGF-B Chains (FIGS. 4A and B)

As described under 1.2, the complete encoding cDNA for the PDGF-B precursor (Ratner et al., 1985) is present in the vector pGEM2-PDGF-B. The complete cDNA sequence of the short variant of the PDGF-A chain (Betsholtz et al., 1986) is contained in the expression vector pODA (Eichner et al., 1989). This vector was obtained by cloning the RsaI fragment from pPGF-1 (Hoppe et al., 1987) into the SV40 expression vector pBEH (Artelt et al., 1988).

The cDNA sequences encoding the PDGF-A and PDGF-B chains were inserted into the monocistronic vectors pSBC-1 and pSBC-2 using EcoRI/HindIII restrictions (FIG. 4). The fusion of the two vectors to form a bicistronic expression unit was carried out using the restriction enzymes XmnI/NotI.

2.4 Preparation of Transformed BHK Cells

Transfection of the monocistronic and bicistronic expression vectors, which carry the sequences encoding the A and B chains of PDGF (cf. FIGS. 1, 4A+B), into BHK cells was carried out using the calcium phosphate precipitation technique (Wigler et al., 1979; Graham and van der Eb, 1973). One day before the transfection, 2–3×10$^5$ BHK cells/24 cm$^2$ were transferred into new culture flasks. At four hours prior to the transfection, a medium exchange was carried out using DME medium. 5 µg of the abovementioned plasmid DNA were suspended in 250 µl of 250 mM CaCl$_2$ together with 0.5 µg of the selection plasmids pAG60 and pSVpac (Colbère-Garapin, 1981; Vara et al., 1986), which encode a gene for neomycin resistance and puromycin resistance, respectively. The solution was slowly added, while being constantly swirled by blowing in sterile air, to 250 µl of 2×HEPES buffer (280 mM NaCl; 50 mM HEPES; 1.5 mM NaH$_2$PO$_4$ pH 7.1) and the resulting precipitate was then added to the nutrient medium. Two days after the transfection, selection for stably transfected cells was begun by changing the medium from DME medium to double-selection medium (5 µg/ml puromycin; 500 µg/ml G418, Wirth et al., 1988), and a population of PDGF-secreting cell clones was obtained. A representative clone mixture of these cells was deposited with the DSM on Aug. 11, 1992 under the number DSM ACC2045.

2.5 Northern Blot Analysis

Figure 5:
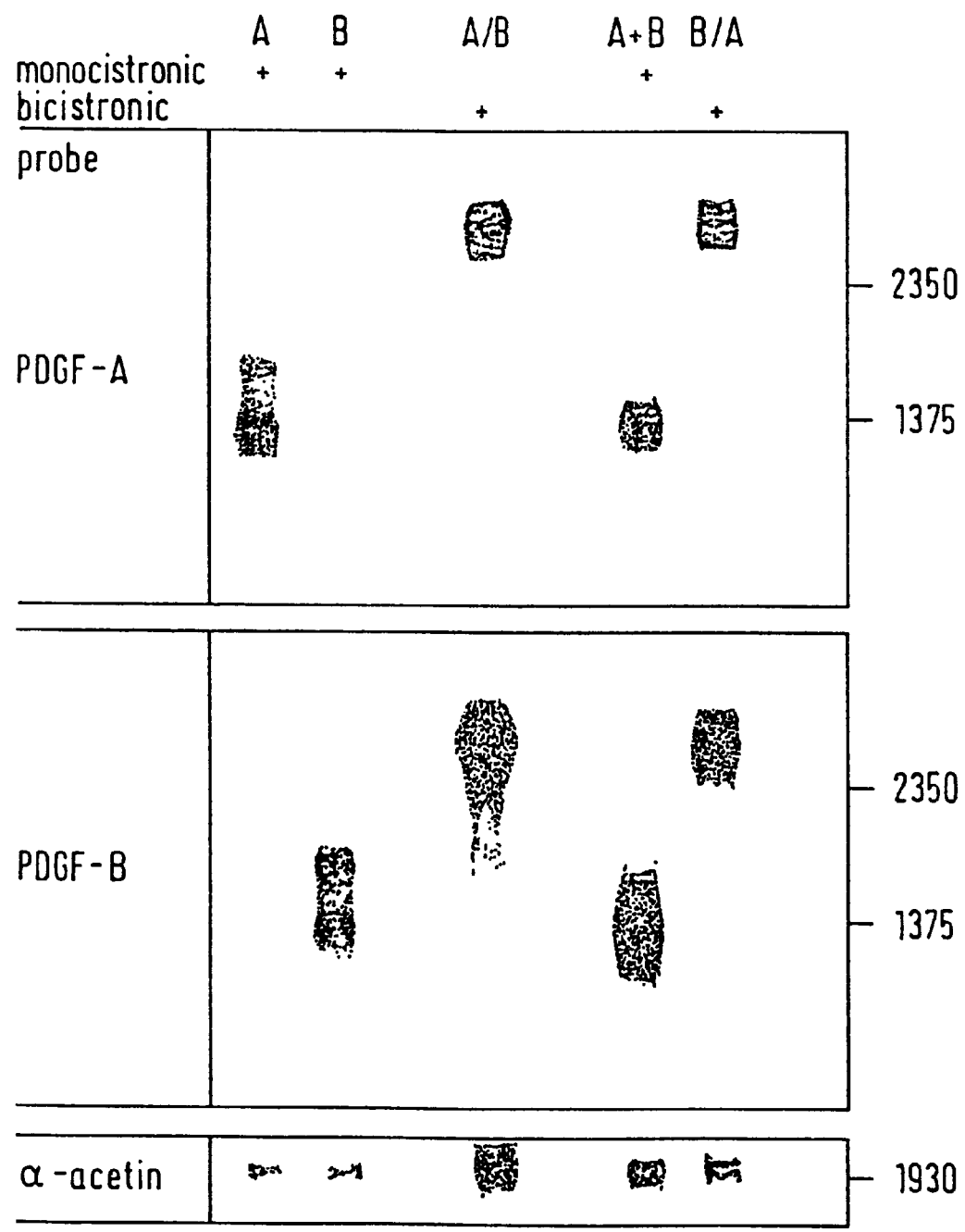
FIG. 5) Northern Blot analysis of transformed BHK cells. An examination was carried out of the mRNA from the total pool of the BHK cells which had been stably transfected with the monocistronic or bicistronic PDGF expression constructs. In accordance with expectation, the monocistronic mRNA's have a size of about 1,300 nt, while the bicistronic mRNA's have the size of the coding sequences of the two PDGF chains (2,500 nucleotides). This demonstrates that the corresponding gene products are read off from a single bicistronic mRNA. The murine α-actin sample was used as a reference [Minty, A. J. et al., J. Biol. Chem. 256, 1008–1014, (1981)].

Polyadenylated RNA from transformed BHK cells was isolated by the method of Purchio et al., (1979), fractionated on a 1% agarose formaldehyde gel (Lehrach et al., 1977), blotted onto a nylon membrane and hybridized with [$^{32}$P]-labelled PDGF-A and PDGF-B chain-specific probes (FIG. 5).

2.6 Preparation of Conditioned Cell Culture Supernatants

The BHK cells were transformed in analogy with 2.4. After counting the colonies, the cells were trypsinized off then taken up in fresh selection medium and adjusted to a cell density of 10$^5$ cells/ml. 10 ml of this cell suspension were in each case transferred into a flask having a floor area of 65 cm$^2$ and cultivated for a further 48 h. After that, the medium was taken off and replaced with 10 ml production medium (DHEM), without serum and selective antibiotics. After 24 h the medium was taken off and replaced with serum-containing selection medium. The harvested supernatants were stored at −20° C. until analyzed. At the time of harvesting, the number of cells/flask was 0.8–1.2×10$^7$.

2.7 Detection of PDGF in the Culture Supernatants Using the Mitogen Test

The mitogenic activity of PDGF can be determined by measuring stimulation of the rate of synthesis of DNA in density-arrested fibroblasts. It is not possible to distinguish between the isoforms in this test.

The assay was carried out in accordance with Shipley et al. (1984) using AKR-2B mouse fibroblasts in 24-well plates. In the test, pure PDGF exhibits half-maximum stimulation at a concentration of about 5 ng/ml. This value was used in order to determine productivities. The results of the mitogen test are compared in FIG. 7 with the values from the PDGF-AB ELISA.

2.8 Detection of PDGF-AB Heterodimer in the Culture Supernatants Using a Specific PDGF-AB ELISA A 'two-antibody sandwich assay' was constructed which permits specific quantification of PDGF-AB in the presence of PDGF-AA and PDGF-BB.

Sandwich assay using a monoclonal and a polyclonal anti-PDGF antibody:

96-well polystyrene plates (from Dynatech, U-Platte No. M124B) are coated in the following sequence (in each case, washing 4× with PBS containing 0.05% Tween 20 between each step):

1) Sheep anti-mouse IgG (from Boehringer Mannheim, No. 1097 105), 3 µg/ml.
2) 1% BSA (from E. Merck, No. 12018) in PBS, pH 7.5, 100 µl, at R.T. for 1 h.
3) Mouse hybridoma supernatant from clone 1B3 [obtained by fusing SP2/0 myeloma cells with spleen cells from mice which had been immunized with recombinant PDGF-AB (from *E. coli* in accordance with Hoppe et al. (1990)], 2 µg/ml IgG2a/ml. The monoclonal antibody binds specifically to the B chain of PDGF dimers.
4) PDGF-containing solutions, diluted in PBS containing 0.1% BSA and 0.05% Tween 20 (PBS+), 50 µl at R.T. for 1 h.
5) Polyclonal rabbit anti-PDGF-AA IgG (from Genzyme, No. ZP-214, binds to the A chain of dimeric PDGF), 2 µg/ml in PBS+, 50 µl at R.T. for 1 h.
6) POD-labelled goat anti-rabbit IgG (from Pierce, No. 31460), 0.1 µg/ml in PBS+, 50 µl at R.T. for 1 h. Detection using the substrate tetramethylbenzidine in accordance with E.S. BOS et al. (J. Immunoassay 2 (1981), 187–204).

2.8.1 Results

The results of three different analyses of PDGF from culture supernatants of recombinant BHK cells are presented in FIG. 7.

The mitogen test provides a serviceable value for the total quantity of rPDGF present in the culture supernatants, without being able to differentiate between the different isoforms (PDGF-AA, PDGF-AB or PDGF-BB).

The specific proportion of heterodimeric PDGF-AB can be determined with a satisfactorily high degree of accuracy by the PDGF-AB-specific ELISA. The percentage proportion of PDGF homodimers may be calculated from the difference between the result of the mitogen test and that of this latter analysis (Table 1).

The result of the ELISA shows that it is only in culture supernatants from transfected cell lines of the type pSBC-PDGF-B/A that a measurable biological activity in the mitogen test is correlated with high PDGF-AB values.

2.9 Purification of the Secreted PDGF-AB

A process developed for purifying rPDGF-AA from cell culture supernatants (Eichner et al., 1989) was employed for purifying the secretion products from 1.5–2.5 liters of conditioned culture supernatants from the different transfection cell pools. The PDGF, which was highly purified or partially purified after the HPLC step, was fractionated on a Laemmli (1970) polyacrylamide gel in the presence of SDS and analyzed after subsequent staining with Coomassie blue (FIG. 8).

2.10 Amino-terminal Sequencing of PDGF Polypeptides

Figure 8:
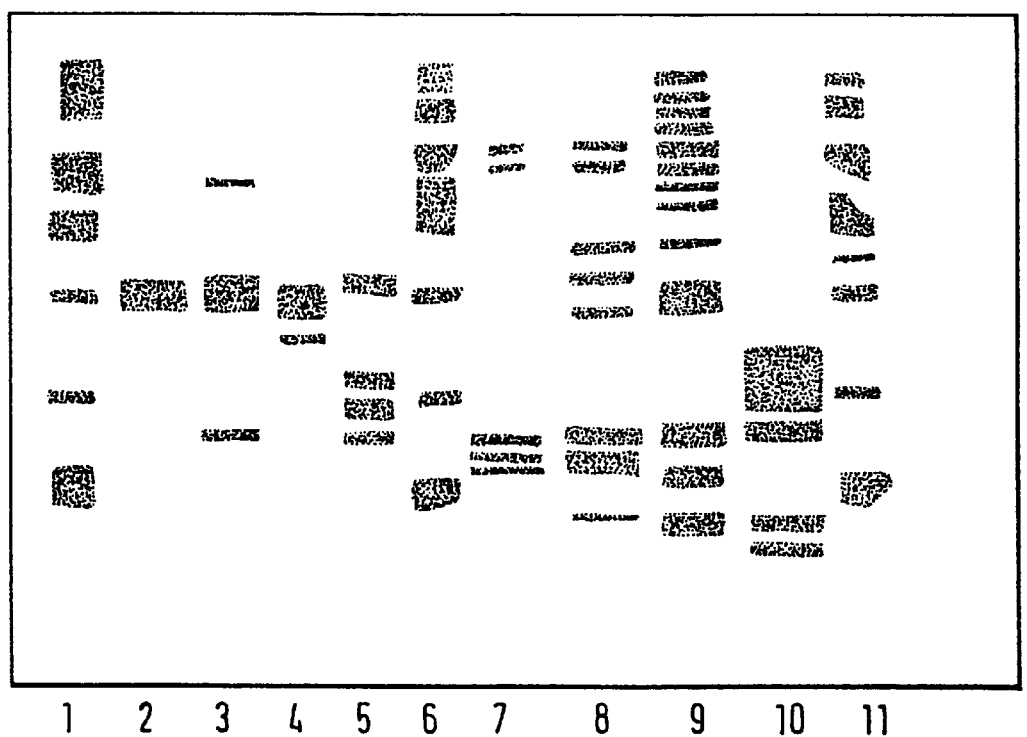

The intention was to identify the two PDGF chains unambiguously by protein sequence analysis in order to exclude the possibility that truncated, processed forms of only one PDGF chain might be present in this case (see FIG. 8).

Automatic sequence analysis was carried out on a 477A model (Applied Biosystems) using the BLOTT1 cycle. The phenylthiohydantoin amino acid derivatives were analyzed on a 120A PTH analyzer, which was coupled online.

The disulphide bridges of the sample are reduced with dithiothreitol and alkylated with 4-vinylpyridine. It is then separated on a horizontal SDS electrophoresis gel in accordance with Schägger and von Jagow, modified as described (Westermeier et al. SD 092/89, Pharmacia LKB Biotechnology). The sample is blotted onto a PVDF membrane (Problot, Applied Biosystems) using a discontinuous buffer system as described (Westermeier et al. SDRE-072, Pharmacia LKB Biotechnology) and then stained with Coomassie Brilliant-Blue R250. The two double bands at 17 and 16 KD are cut out and sequenced together.

Based on the results of the protein determination, 10 μg of sample were analyzed. It was possible to detect the N-terminal amino acids of the PDGF-A and PDGF-B chains in equivalent yield (Table 2). Contaminating sequences were not detected.

TABLE 2

Amino acid sequence analysis of the PDGF-A and PDGF-B chains

| | PDGF-A | | PDGF-B | |
|---|---|---|---|---|
| Cycle | Code | Yield (pmol) | Code | Yield (pmol) |
| 1 | Ser | 101.1* | Ser | |
| 2 | Ile | 75.7 | Leu | 89.7 |
| 3 | Glu | 58.8 | Gly | 82.0 |
| 4 | Glu | 67.2 | Ser | 42.9 |
| 5 | Ala | 55.7 | Leu | 70.2 |
| 6 | Val | 61.0 | Thr | 59.4 |
| 7 | Pro | 45.9 | Ile | 65.4 |
| 8 | Ala | 104.6* | Ala | |
| 9 | Val | 46.8 | Glu | 49.9 |
| 10 | Cys | 40.5 | Pro | 31.8 |
| 11 | Lys | 24.1 | Ala | 34.6 |
| 12 | Thr | 23.5 | Met | 16.5 |
| 13 | Arg | 30.3 | Ile | 25.2 |
| 14 | Thr | 24.7 | Ala | 29.2 |
| 15 | Val | 17.5 | Glu | 28.6 |
| 16 | Ile | 27.5 | Cys | 23.2 |
| 17 | Tyr | 16.4 | Lys | 11.2 |
| 18 | Glu | 20.9 | Thr | 13.4 |
| 19 | Ile | 24.8 | Arg | 20.9 |
| 20 | Pro | 17.1 | Thr | 16.9 |
| 21 | Arg | 29.0 | Glu | 16.7 |
| 22 | | | Val | 19.8 |
| 23 | Gln | 8.1 | Phe | 10.2 |

*Yield from both chains

Abbreviations

BHK—Hamster cell line (baby hamster kidney)
bp—base pair(s)
CHO—Hamster cell line (Chinese hamster ovary)
BSA—Bovine serum albumin
D—Dalton
DMEM—Dulbecco's modified Eagle medium
ELISA—enzyme-linked immunosorbent assay
HEPES—4-(2-hydroxyethyl)-1-piperazineethanesulphonic acid
HPLC—high pressure liquid chromatography
IgG—class G immunoglobulin
IRES—internal ribosomal entry site
nt—nucleotide(s)
PAGE—polyacrylamide gel electrophoresis
PBS—phosphate-buffered sodium chloride solution
PCR—polymerase chain reaction
PDGF—platelet-derived growth factor
POD—peroxidase
PVDF—polyvinylidene fluoride
SDS—sodium dodecyl sulphate
UTR—untranslated-region

TABLE 1

| | pSBC-A/B | pSBC-B/A | pSBC-2-PDGF-A + pSBC-2-PDGF-B | pSBC-2-PDGF-A | pSBC-2-PDGF-B | pSBC control |
|---|---|---|---|---|---|---|
| PDGF [ng/ml] (mitogen test) | 600 | 550 | 900 | 1000 | 250 | 0 |
| PDGF-AB [ng/ml] (PDGF-AB-ELISA] | 240 | 520 | 600 | 30 | 10 | 10 |
| Proportion of PDGF-AB | 40 | 95 | 56 | 3 | 4 | 0 |

Literature

Adam M. A., Ramesh N., Miller A. D., and Osborne W. R. A. (1991) J. Virol. 65, 4985–4990.

Artelt P., Morelle C., Ausmeier M., Fitzek M., and Hauser H. (1988) Gene 68, 213–219.

Beckmann M. P., Betsholtz C., Heldin C.-H., Westermark B., Di Marco E., Di. Fiore P. P., Robbins K. C., and Aaronson S. A. (1988) Science 241, 1344–1349.

Betsholtz C., Johnsson A., Heldin C.-H., Westermark B., Lind P., Urdea M. S., Eddy R., Shows T. B., Philpott K., Mellor A. L., Knott T. J., and Scott J. (1986) Nature 320, 695–699.

Block L. H., Emmons L. R., Vogt E., Sachinidis A., Vetter W., and Hoppe J. (1989) Proc. Natl. Acad. Sci. USA 86, 2388–2392.

Boel E., Berkner K. L., Nexoe B. A., and Schwartz T. W. (1987) FEBS Lett. 219, 181–188.

Bywater M., Rorsman F., Bongcam-Rudloff E., Mark G., Hammacher A., Heldin C.-H., Westermark B., and Betsholtz C. (1988) Mol. Cell. Biol. 8, 2753–2762.

Colbére-Garapin F., Horodniceanu F., Kourilsky P., and Garapin A. C. (1981) J. Mol. Biol. 150, 1–14.

Eichner W., Jäger V., Herbst D., Hauser E. and Hoppe J. (1989) Eur. J. Biochem. 185, 135–140.

Falcone D., and Andrews D. W. (1991) Mol. Cell. Biol. 11 (5), 2656–2664.

Ghattas I. R., Sanes J. R., and Majors J. E. (1991) Mol. Cell. Biol. 22, 5848–5859.

Graham F., and van der Eb L. (1973) Virology 52, 456–487.

Hambidge S. J., and Sarnow P. (1991) J. Virol. 65, 6312–6315.

Hammacher A., Hellmann U., Johnsson A., Östman A., Gunnarsson K., Westermark B., Wasteson A., and Heldin C.-H. (1988) J. Biol. Chem. 263, 16493–16499.

Hart C. E., Forstrom J. W., Kelly J. D., Seifert R. A., Smith R. A., Ross R., Murray M. J., and Bowen-Pope D. F. (1988) Science 240, 1529–1531.

Hart C. E., Bailey M., Curtis D. A., Osborn S., Raines E., Ross R., and Forstrom J. W. (1990) Biochemistry 29, 166–172.

Heldin C.-H., Johnsson A., Wennergren S., Wernstedt C., Betsholtz C., and Westermark B. (1986) Nature 319, 511–514.

Heldin C.-H., Bäckström G., Östman A., Hammacher A., Rönnstrand L., Rubin K., Nister M., and Westermark B. (1988) EMBO J. 7, 1387–1393.

Hoppe J., Schumacher L., Eichner W. and Weich H. A. (1987), FEBS Lett. 223, 243–246.

Hoppe J., Weich H. A., and Eichner W. (1989) Biochemistry 28, 2956–2960.

Hoppe J., Weich H. A., and Eichner W., and Tatje D. (1990) Eur. J. Biochem. 187, 207–214.

Hosang M., Rouge M., Wipf B., Eggiman B., Kaufmann F., and Hunziker W. (1989) J. Cell. Physiol. 149, 558–564.

Jackson R. J., Howell M. T., and Kaminski A. (1990) Trends Biochem. Sci. 15, 477–483.

Jang S. K., Kräusslich E., Nicklin M. J. E., Duke G. M., Palmenberg A. C., and Wimmer E. (1988) J. Virol. 62, 2636.

Jang S. K., Davies M. V., Kaufmann R. J., and Wimmer E. (1989) J. Virol. 63 (4), 1651–1660.

Jang S. K., and Wimmer E. (1990) Genes Dev. 4, 1560–1572.

Johnsson A., Heldin C.-E., Wasteson A., Westermark B., Deuel T. F., Huang J. S., Seeburg P. H., Gray A., Ullrich A., Scrace G., Stroobant P., Waterfield M. D. (1984) EMBO J. 136, 921–928.

Kaufman R. J., Murtha P., and Davies M. V. (1987) EMBO J. 6, 187–193.

Kaufman R. J., Davies M. V. Wasley L. C., and Michnick D. (1991) Nucleic Acids Res. 19, 4485–4490.

Kelly J. D., Raines E. W., Ross R., and Murray M. J. (1985) EMBO J. 4, 3399–3405.

Kolvenbach C. G., Langley K. B., Strickland T. W., Kenney W. C., and Arakawa T. (1991) J. Biochem. Biophys. Meth. 23, 295–300.

Kozak M. (1987) Mol. Cell. Biol. 7 (10), 3438–3445.

Kozak M. (1989) Mol. Cell. Biol. 9, 5134–5142.

Laemmli U. K. (1970) Nature 227, 680–685.

Lehrach H., Diamond D., Wozney J. M., and Boedtker E. (1977) Biochemistry 16, 4743–4751.

Macejak D. G., and Sarnow P. (1991) Nature (London) 353, 90–94.

Matoskova B., Rorsman F., Svensson V. and Betsholtz C. (1989), Mol. Cell. Biol. 9, 3148–3150.

Meerovitch K., Pelletier J., and Sonenberg N. (1989) Genes Dev. 3, 1026–1034.

Nister M., Hammacher A., Mellström K., Siegbahn A., Rönnstrang L., Westermark B., and Heldin C.-H. (1988); Cell 52, 791–799.

Östman A., Rall L., Hammacher A., Wormstead M. A., Coit D., Valenzuela P., Betsholtz C., Westermark B., and Heldin C.-H. (1988) J. Biol. Chem. 263, 16202–16208.

Pelletier J., and Sonenberg N. (1988) Nature 334, 320.

Purchio A. F. and Fareed G. C. (1979) J. Virol. 29, 763–769.

Ratner L., Josephs S. F., Jarrett R., Reitz M. S. and Wong-Staal F. (1985), Nucl. Acids Res. 13, 5007–5018.

Reilly C. F. and Broski J. E. (1989) Biochem. Biophys. Res. Commun. 160, 1047–1054.

Sachinidis A., Locher R., Vetter W., Tatje D., and Hoppe J. (1990) J. Biol. Chem. 265, 10238–10243.

Sachinidis A., Locher R., Hoppe J., and Vetter W. (1990) FEBS Lett. 275, 95–98.

Sarnow P. (1989) J. Virol. 63, 467–470.

Shipley G. D., Childes C. B., Volkenant M. E. and Moses H. L. (1984) Cancer Res. 44, 710–716.

Siegbahn A., Hammacher A., Westermark B., and Heldin C.-H. (1990) J. Clin. Invest. 85, 916–920.

Simoes E. A. F., and Sarnow P. (1991) J. Virol. 65, 913–921.

Stroobant P., and Waterfield M. D. (1984) EMBO J. 3, 2963–2967.

Vara J., Portela A., Oritin J. and Jimenez A. (1986) Nucl. Acids Res. 14, 4617–4624.

Weich H. A., Sebald W., Schairer H. U., and Hoppe J. (1986), FEBS Lett. 198, 344–348.

Wigler M., Sweet R., Sim G. K., Wold B., Pellicer A., Lacy E., Maniatis T., Silverstein S., and Axel R. (1979) Cell 16, 777–785.

Wirth M., Bode J., Zettlmeiβl G., and Hauser H. (1988) Gene 73, 419–426.

Wirth M., Schumacher L., and Hauser H. (1991) In Modern Approaches to Animal Cell Technology, Griffiths B., Spier R., and Meigner R., eds. Butterworths), pp. 338–343.

Wise R. J., Orkin S. H. and Collins T. (1989) Nucl. Acids Res. 17, 6591–6601.

Wood C. R., Morris G. E., Alderman E. M., Fouser L., and Kaufman R. J. (1991) Proc. Natl. Acad. Sci. USA 88, 8006–8010.

Young R. M., Mendoza A. E., Collins T. and Orkin S. H. (1990) Mol. Cell. Biol. 10, 6051–6054.

We claim:

1. A process for the preparation of a pharmaceutical preparation comprising a recombinant platelet derived growth factor AB (rPDGF-AB), characterized in that mammalian cells, as host cells which harbor an expression unit of the general formula $$p\text{-}5'UTR\text{-}C_1\text{-}IRES\text{-}C_2\text{-}3'UTR\text{-}polyA,$$

inserted in an operative manner, in which p is a transcriptional promoter,

5'UTR (5'untranslated region) is an untranslated nucleotide sequence, $C_1$ is a cistron encoding the B chain of PDGF, a biologically active analog, or a biologically active fragment thereof, IRES is a nucleotide sequence of viral, cellular or synthetic origin, which sequence mediates an internal binding of the ribosomes, $C_2$ is a cistron encoding the A chain of PDGF or a biologically active analog, or a biologically active fragment thereof, 3'UTR (3'untranslated region) is an untranslated nucleotide sequence, and polyA is a polyadenylation signal, where $C_1$, IRES (Internal Ribosomal Entry Site) and $C_2$ are connected to each other in an operative manner, are cultivated in a suitable medium, the resulting rPDGF-AB is separated from the cells and the medium and is formulated together with a pharmaceutically tolerable auxiliary agent or excipient.

2. A process according to claim 1, characterized in that $C_1$ contains the complete PDGF-B precursor sequence (SEQ ID No: 3), an allelic variant or fragment thereof, which encodes a biologically active PDGF-B chain.

3. A process according to claim 2, characterized in that $C_1$ contains the v-sis gene from simian sarcoma virus or the base pairs 283 to 609 according to SEQ ID NO: 3.

4. A process according to claim 1, characterized in that $C_2$ contains the PDGF-$A_K$-(SEQ ID NO: 1) or the PDGF-$A_L$ precursor sequence.

5. A process according to claim 1, characterized in that the IRES has the nucleotide sequence according to SEQ ID NO: 5.

6. A process according to claim 1, characterized in that the IRES is the 5'UTR of a member selected from the group consisting of encephalomyocoarditis virus (EMV), "Theiler's murine encephalomyelitis virus" (TMEV), "foot and mouth disease virus" (FMDV), "bovine enterovirus" (BEV), coxsackie B virus (CBV), "human rhinovirus" (HRV), "human immunoglobulin heavy chain binding protein" (BIP) 5'UTR, Drosophila antennapediae 5'UTR, Drosophila ultrabithorax 5'UTR, or a genetic hybrid or fragment thereof, wherein the genetic hybrid or fragment mediates the internal binding of the ribosomes.

7. A process according to claim 1, characterized in that the host cell is a CHO or BHK cell.

8. A process according to claim 7, characterized in that the host cell is a BHK cell and is derived from the clone 91-24-4D having the deposition number DSM ACC2045.

* * * * *

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
          (A) LENGTH: 748 base pairs
          (B) TYPE: nucleic acid
          (C) STRANDEDNESS: single
          (D) TOPOLOGY: linear (ii) MOLECULE TYPE: cDNA (vi) ORIGINAL SOURCE:
          (A) ORGANISM: Homo sapiens (vii) IMMEDIATE SOURCE:
          (B) CLONE: pODA (Eichner et al., 1989)

(ix) FEATURE:
          (A) NAME/KEY: CDS
          (B) LOCATION: 95..682
          (D) OTHER INFORMATION: /product= "PDGF-A precursor sequence
               (short splice form)"
               /note= "human PDGF-A gene (short splice form, [2])
               from pODA, flanked by 5'-EcoRI and 3'-HindIII
               restriction cleavage sites"
               /citation= ([2])

(ix) FEATURE:
          (A) NAME/KEY: mat_peptide
          (B) LOCATION: 353..682
          (D) OTHER INFORMATION: /product= "mature PDGF-A chain"

(x) PUBLICATION INFORMATION:
          (A) AUTHORS: Eichner, W.
               Jaeger, V.
               Herbst, D.
               Hauser, H.
               Hoppe, J.
          (C) JOURNAL: Eur. J. Biochem.
          (D) VOLUME: 185
          (F) PAGES: 135-140
          (G) DATE: 1989

(x) PUBLICATION INFORMATION:
          (A) AUTHORS: Hoppe, J.
               Schumacher, L.
               Eichner, W.
               Weich, H. A.
          (C) JOURNAL: FEBS Lett.
          (D) VOLUME: 223
          (F) PAGES: 243-246
          (G) DATE: 1987

(xi) SEQUENCE DESCRIPTION: SEQ ID NO: 1:

```
GAATTCCCAC TGAATTTCGC CGCCACAGGA GACCGGCTGG AGCGCCCGCC CC
GCGCCTCG        60

CCTCTCCTCC GAGCAGCCAG CGCCTCGGGA CGCG ATG AGG ACC T
TG GCT TGC        112
                    Met Arg Thr Leu Ala Cys
                     -86  -85

CTG CTG CTC CTC GGC TGC GGA TAC CTC GCC CA
T GTT CTG GCC GAG GAA        160
Leu Leu Leu Leu Gly Cys Gly Tyr Leu Ala Hi
s Val Leu Ala Glu Glu
 -80       -
 75                -
 70                -
 65

GCC GAG ATC CCC CGC GAG GTG ATC GAG AGG CT
G GCC CGC AGT CAG ATC        208
Ala Glu Ile Pro Arg Glu Val Ile Glu Arg Le
u Ala Arg Ser Gln Ile
              -60
                  -55
                      -50

CAC AGC ATC CGG GAC CTC CAG CGA CTC CTG GA
G ATA GAC TCC GTA GGG        256
His Ser Ile Arg Asp Leu Gln Arg Leu Leu Gl
u Ile Asp Ser Val Gly
              -45
                  -40
                      -35

AGT GAG GAT TCT TTG GAC ACC AGC CTG AGA GC
T CAC GGG GTC CAC GCC        304
Ser Glu Asp Ser Leu Asp Thr Ser Leu Arg Al
a His Gly Val His Ala
              -30
                  -25
                      -20

ACT AAG CAT GTG CCC GAG AAG CGG CCC CTG CC
C ATT CGG AGG AAG AGA        352
Thr Lys His Val Pro Glu Lys Arg Pro Leu Pr
o Ile Arg Arg Lys Arg
     -15
         -10
             -5

AGC ATC GAG GAA GCT GTC CCC GCT GTC TGC AA
G ACC AGG ACG GTC ATT        400
Ser Ile Glu Glu Ala Val Pro Ala Val Cys Ly
s Thr Arg Thr Val Ile
       1             5
                         10
                             15

TAC GAG ATT CCT CGG AGT CAG GTC GAC CCC AC
G TCC GCC AAC TTC CTG        448
Tyr Glu Ile Pro Arg Ser Gln Val Asp Pro Th
r Ser Ala Asn Phe Leu
              20
                  25
                      30

ATC TGG CCC CCG TGC GTG GAG GTG AAA CGC TG
C ACC GGC TGC TGC AAC        496
Ile Trp Pro Pro Cys Val Glu Val Lys Arg Cy
s Thr Gly Cys Cys Asn
              35
                  40
                      45
```

```
ACG AGC AGT GTC AAG TGC CAG CCC TCC CGC GT
C CAC CAC CGC AGC GTC       544
Thr Ser Ser Val Lys Cys Gln Pro Ser Arg Va
l His His Arg Ser Val
        50
            55
                60

AAG GTG GCC AAG GTG GAA TAC GTC AGG AAG AA
G CCA AAA TTA AAA GAA       592
Lys Val Ala Lys Val Glu Tyr Val Arg Lys Ly
s Pro Lys Leu Lys Glu
 65
    70
        75
            80

GTC CAG GTG AGG TTA GAG GAG CAT TTG GAG TG
C GCC TGC GCG ACC ACA       640
Val Gln Val Arg Leu Glu Glu His Leu Glu Cy
s Ala Cys Ala Thr Thr
                85
                    90
                        95

AGC CTG AAT CCG GAT TAT CGG GAA GAG GAC AC
G GAT GTG AGG
 682
Ser Leu Asn Pro Asp Tyr Arg Glu Glu Asp Th
r Asp Val Arg
            100
                105
                    110

TGAGGATGAG CCGCAGCCCT TTCCTGGGAC ATGGATGTGG GGATCCGTCG AC
CTGCAGCC        742

AAGCTT

748

(2) INFORMATION FOR SEQ ID NO: 2:

(i) SEQUENCE CHARACTERISTICS:
        (A) LENGTH: 196 amino
acids
        (B) TYPE: amino acid
        (D) TOPOLOGY: linear (ii) MOLECULE TYPE: protein (xi) SEQUENCE DESCRIPTION: SEQ
ID NO: 2:

Met Arg Thr Leu Ala Cys Leu Leu Leu Leu Gl
y Cys Gly Tyr Leu Ala
-86 -85
                                    -80
 -75

His Val Leu Ala Glu Glu Ala Glu Ile Pro Ar
g Glu Val Ile Glu Arg
-70                             -
65                                  -
60                                      -
55

Leu Ala Arg Ser Gln Ile His Ser Ile Arg As
p Leu Gln Arg Leu Leu
            -50
                -45
                    -40

Glu Ile Asp Ser Val Gly Ser Glu Asp Ser Le
u Asp Thr Ser Leu Arg
                -35
                    -30
                        -25
```

Ala His Gly Val His Ala Thr Lys His Val Pro Glu Lys Arg Pro Leu
         -20
             -15
                 -10

Pro Ile Arg Arg Lys Arg Ser Ile Glu Glu Ala Val Pro Ala Val Cys
       -5
          1
    5
  10

Lys Thr Arg Thr Val Ile Tyr Glu Ile Pro Arg Ser Gln Val Asp Pro
                15
                   20
                      25

Thr Ser Ala Asn Phe Leu Ile Trp Pro Pro Cys Val Glu Val Lys Arg
                30
                   35
                      40

Cys Thr Gly Cys Cys Asn Thr Ser Ser Val Lys Cys Gln Pro Ser Arg
                45
                   50
                      55

Val His His Arg Ser Val Lys Val Ala Lys Val Glu Tyr Val Arg Lys
       60
          65
             70

Lys Pro Lys Leu Lys Glu Val Gln Val Arg Leu Glu Glu His Leu Glu
 75
 80
 85
 90

Cys Ala Cys Ala Thr Thr Ser Leu Asn Pro Asp Tyr Arg Glu Glu Asp
                    95
                       100
                          105

Thr Asp Val Arg
           110

(2) INFORMATION FOR SEQ ID NO: 3:

(i) SEQUENCE CHARACTERISTICS:
        (A) LENGTH: 868 base
pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapi
ens (vii) IMMEDIATE SOURCE:
        (B) CLONE: pMVW-2 (Weic
h et al., 1986)

(ix) FEATURE:
        (A) NAME/KEY: CDS
        (B) LOCATION: 40..762
        (D) OTHER INFORMATION:
/product= "PDGF-B
            precursor

```
                sequence"
                           /note=
"human PDGF-B gene from pGEM2-PDGF-B,
                        flanked b
y 5'-EcoRI und 3'-HindIII
                        restriction
cleavage sites"

(ix) FEATURE:
            (A) NAME/KEY: mat_
peptide
            (B) LOCATION: 283..609
            (D) OTHER INFORMATION:
/product= "mature PDGF-B chain"

(x) PUBLICATION INFORMATION:
            (A) AUTHORS: Weich, H.
A.
                         Sebald, W
.
                         Schairer,
H. U.
                         Hoppe, U.
            (C) JOURNAL: FEBS Lett.
            (D) VOLUME: 198
            (F) PAGES: 344-348
            (G) DATE: 1986

(xi) SEQUENCE DESCRIPTION: SEQ
ID NO: 3:

GAATTCGAGC TCGCCCGGGG ATCCTCTAGA GTCGACACC ATG AAT CGC
 TGC TGG         54

Met Asn Arg Cys Trp

-81  -80

GCG CTC TTC CTG TCT CTC TGC TGC TAC CTG CG
T CTG GTC AGC GCC GAG        102
Ala Leu Phe Leu Ser Leu Cys Cys Tyr Leu Ar
g Leu Val Ser Ala Glu
       -75
         -70
           -65

GGG GAC CCC ATT CCC GAG GAG CTT TAT GAG AT
G CTG AGT GAT CAC TCG        150
Gly Asp Pro Ile Pro Glu Glu Leu Tyr Glu Me
t Leu Ser Asp His Ser
-60                              -
55                          -
50                     -
45

ATC CGC TCC TTT GAT GAT CTC CAA CGC CTG
CTG CAC GGA GAC CCC GGA       198
Ile Arg Ser Phe Asp Asp Leu Gln Arg Leu Le
u His Gly Asp Pro Gly
               -40
                  -35
                     -30

GAG GAA GAT GGG GCC GAG TTG GAC CTG AAC AT
G ACC CGC TCC CAC TCT        246
Glu Glu Asp Gly Ala Glu Leu Asp Leu Asn Me
t Thr Arg Ser His Ser
                     -25
                        -20
                           -15

GGA GGC GAG CTG GAG AGC TTG GCT CGT GGA AG
A AGG AGC CTG GGT TCC        294
Gly Gly Glu Leu Glu Ser Leu Ala Arg Gly Ar
g Arg Ser Leu Gly Ser
            -10
               -5
                1
```

```
CTG ACC ATT GCT GAG CCG GCC ATG ATC GCC GA
G TGC AAG ACG CGC ACC         342
Leu Thr Ile Ala Glu Pro Ala Met Ile Ala Gl
u Cys Lys Thr Arg Thr
  5
                10
                        15
                                20

GAG GTG TTC GAG ATC TCC CGG CGC CTC ATA GA
C CGC ACC AAC GCC AAC         390
Glu Val Phe Glu Ile Ser Arg Arg Leu Ile As
p Arg Thr Asn Ala Asn
                    25
                            30
                                    35

TTC CTG GTG TGG CCG CCC TGT GTG GAG GTG CA
G CGC TGC TCC GGC TGC         438
Phe Leu Val Trp Pro Pro Cys Val Glu Val Gl
n Arg Cys Ser Gly Cys
            40
                    45
                            50

TGC AAC AAC CGC AAC GTG CAG TGC CGC CCC AC
C CAG GTG CAG CTG CGA         486
Cys Asn Asn Arg Asn Val Gln Cys Arg Pro Th
r Gln Val Gln Leu Arg
        55
                60
                        65

CCT GTC CAG GTG AGA AAG ATC GAG ATT GTG CG
G AAG AAG CCA ATC TTT         534
Pro Val Gln Val Arg Lys Ile Glu Ile Val Ar
g Lys Lys Pro Ile Phe
    70
            75
                    80

AAG AAG GCC ACG GTG ACG CTG GAA GAC CAC CT
G GCA TGC AAG TGT GAG         582
Lys Lys Ala Thr Val Thr Leu Glu Asp His Le
u Ala Cys Lys Cys Glu
 85
 90
 95
100

ACA GTG GCA GCT GCA CGG CCT GTG ACC CGA AG
C CCG GGG GGT TCC CAG         630
Thr Val Ala Ala Ala Arg Pro Val Thr Arg Se
r Pro Gly Gly Ser Gln
            105
                    110
                            115

GAG CAG CGA GCC AAA ACG CCC CAA ACT CGG GT
G ACC ATT CGG ACG GTG         678
Glu Gln Arg Ala Lys Thr Pro Gln Thr Arg Va
l Thr Ile Arg Thr Val
        120
                125
                        130

CGA GTC CGC CGG CCC CCC AAG GGC AAG CAC CG
G AAA TTC AAG CAC ACG         726
Arg Val Arg Arg Pro Pro Lys Gly Lys His Ar
g Lys Phe Lys His Thr
    135
            140
                    145

CAT GAC AAG ACG GCA CTG AAG GAG ACC CTT GG
A GCC TAGGGGCATC              772
His Asp Lys Thr Ala Leu Lys Glu Thr Leu Gl
y Ala
    150
```

```
                                155
                                160

GGCAGGAGAG TGTGTGGGCA GGGTTATTTA ATATGGTATT TGCTGTATTG CC
CCCATGGC      832

CCAATCGATC CCGTCGACCT GCAGGCATGC AAGCTT

868

(2) INFORMATION FOR SEQ ID NO: 4:

(i) SEQUENCE CHARACTERISTICS:
           (A) LENGTH: 241 amino
acids
           (B) TYPE: amino acid
           (D) TOPOLOGY: linear (ii) MOLECULE TYPE: protein (xi) SEQUENCE DESCRIPTION: SEQ
ID NO: 4:

Met Asn Arg Cys Trp Ala Leu Phe Leu Ser Le
u Cys Cys Tyr Leu Arg
-81 -80
 -75
 -70

Leu Val Ser Ala Glu Gly Asp Pro Ile Pro Gl
u Glu Leu Tyr Glu Met
-65                       -
60                        -
55                        -
50

Leu Ser Asp His Ser Ile Arg Ser Phe Asp As
p Leu Gln Arg Leu Leu
              -45
              -40
              -35

His Gly Asp Pro Gly Glu Glu Asp Gly Ala Gl
u Leu Asp Leu Asn Met
              -30
              -25
              -20

Thr Arg Ser His Ser Gly Gly Glu Leu Glu Se
r Leu Ala Arg Gly Arg
        -15
        -10
         -5

Arg Ser Leu Gly Ser Leu Thr Ile Ala Glu Pr
o Ala Met Ile Ala Glu
          1
          5
         10
         15

Cys Lys Thr Arg Thr Glu Val Phe Glu Ile Se
r Arg Arg Leu Ile Asp
              20
              25
              30

Arg Thr Asn Ala Asn Phe Leu Val Trp Pro Pr
o Cys Val Glu Val Gln
              35
              40
              45

Arg Cys Ser Gly Cys Cys Asn Arg Asn Val
l Gln Cys Arg Pro Thr
              50
              55
              60
```

-continued

Gln Val Gln Leu Arg Pro Val Gln Val Arg Ly
s Ile Glu Ile Val Arg
65
70
75

Lys Lys Pro Ile Phe Lys Lys Ala Thr Val Th
r Leu Glu Asp His Leu
80
85
90
95

Ala Cys Lys Cys Glu Thr Val Ala Ala Ala Ar
g Pro Val Thr Arg Ser
100
105
110

Pro Gly Gly Ser Gln Glu Gln Arg Ala Lys Th
r Pro Gln Thr Arg Val
115
120
125

Thr Ile Arg Thr Val Arg Val Arg Arg Pro Pr
o Lys Gly Lys His Arg
130
135
140

Lys Phe Lys His Thr His Asp Lys Thr Ala Le
u Lys Glu Thr Leu Gly
145
150
155

Ala
160

(2) INFORMATION FOR SEQ ID NO: 5:

(i) SEQUENCE CHARACTERISTICS:
(A) LENGTH: 628 base
pairs
(B) TYPE: nucleic acid
(C) STRANDEDNESS: single
(D) TOPOLOGY: linear (vi) ORIGINAL SOURCE:
(A) ORGANISM: Poliovirus
Typ 1 (Mahoney strain)

(vii) IMMEDIATE SOURCE:
(B) CLONE: pGEM 3-5'
Polio (M) (4708 bp), (Sarnow, 1989)

(ix) FEATURE:
(A) NAME/KEY: -
(B) LOCATION: 1..628
(D) OTHER INFORMATION:
/note= “shown are the first 628 nt of the
5' non-translated region of poliovi
rus Typ 1 (Mahoney)”

(ix) FEATURE:
(A) NAME/KEY: -
(B) LOCATION: 610
(D) OTHER INFORMATION:
/note= “non-authentic sequence
due to
a base pair substitution from C to G
at positi
on 610”

```
            (x) PUBLICATION INFORMATION:
                (A) AUTHORS: Sarnow, P.
                (C) JOURNAL: J. Virol.
                (D) VOLUME: 63
                (F) PAGES: 467-470
                (G) DATE: 1989

(xi) SEQUENCE DESCRIPTION: SEQ
ID NO: 5:

TTAAAACAGC TCTGGGGTTG TACCCACCCC AGAGGCCCAC GTGGCGGCTA GT
ACTCCGGT      60

ATTGCGGTAC CCTTGTACGC CTGTTTTATA CTCCCTTCCC GTAACTTAGA CG
CACAAAAC     120

CAAGTTCAAT AGAAGGGGGT ACAAACCAGT ACCACCACGA ACAAGCACTT CT
GTTTCCCC     180

GGTGATGTCG TATAGACTGC TTGCGTGGTT GAAAGCGACG GATCCGTTAT CC
GCTTATGT     240

ACTTCGAGAA GCCCAGTACC ACCTCGGAAT CTTCGATGCG TTGCGCTCAG CA
CTCAACCC     300

CAGAGTGTAG CTTAGGCTGA TGAGTCTGGA CATCCCTCAC CGGTGACGGT GG
TCCAGGCT     360

GCGTTGGCGG CCTACCTATG GCTAACGCCA TGGGACGCTA GTTGTGAACA AG
GTGTGAAG     420

AGCCTATTGA GCTACATAAG AATCCTCCGG CCCCTGAATG CGGCTAATCC CA
ACCTCGGA     480

GCAGGTGGTC ACAAACCAGT GATTGGCCTG TCGTAACGCG CAAGTCCGTG GC
GGAACCGA     540

CTACTTTGGG TGTCCGTGTT TCCTTTTATT TTATTGTGGC TGCTTATGGT GA
CAATCACA     600

GATTGTTATG ATAAAGCGAA TTGGATTG

628

(2) INFORMATION FOR SEQ ID NO: 6:

(i) SEQUENCE CHARACTERISTICS:
            (A) LENGTH: 17 base
pairs
            (B) TYPE: nucleic acid
            (C) STRANDEDNESS: single
            (D) TOPOLOGY: linear (ix) FEATURE:
            (A) NAME/KEY: -
            (B) LOCATION: 1..17
            (D) OTHER INFORMATION:
/label= M1317MER
             /note=
"synthetic DNA; M13 sequencing primer
        (New England Biolabs Gm
bH), utilized for PCR"

(xi) SEQUENCE DESCRIPTION: SEQ
ID NO: 6:

GTAAAACGAC GGCCAGT

17

(2) INFORMATION FOR SEQ ID NO: 7:

(i) SEQUENCE CHARACTERISTICS:
            (A) LENGTH: 24 base
pairs
            (B) TYPE: nucleic acid
            (C) STRANDEDNESS: single
```

(D) TOPOLOGY: linear (ix) FEATURE:
        (A) NAME/KEY: -
        (B) LOCATION: 1..24
        (D) OTHER INFORMATION:
/label= M1324MER
            /note=
"synthetic DNA; M13 reverse
            sequencing
primer (New England Biolabs GmbH),
            utilized
for PCR"

(xi) SEQUENCE DESCRIPTION: SEQ
ID NO: 7:

AGCGGATAAC AATTTCACAC AGGA

24

(2) INFORMATION FOR SEQ ID NO: 8:

(i) SEQUENCE CHARACTERISTICS:
        (A) LENGTH: 19 base
pairs
        (B) TYPE: nucleic acid
        (C) STRANDEDNESS: single
        (D) TOPOLOGY: linear (ix) FEATURE:
        (A) NAME/KEY: -
        (B) LOCATION: 1..19
        (D) OTHER INFORMATION:
/label= NCCLSA1
            /note=
"synthetic DNA; synthetic linker for
            recloning
of the shortened PDGF-B precursor
            from pMVW
-2 in bacteriophage M13mp19"

(xi) SEQUENCE DESCRIPTION: SEQ
ID NO: 8:

CATGGCCCAA TCGATCCCG

19

(2) INFORMATION FOR SEQ ID NO: 9:

(i) SEQUENCE CHARACTERISTICS:
        (A) LENGTH: 19 base
pairs
        (B) TYPE: nucleic acid
        (C) STRANDEDNESS: single
        (D) TOPOLOGY: linear (ix) FEATURE:
        (A) NAME/KEY: -
        (B) LOCATION: 1..19
        (D) OTHER INFORMATION:
/label= NCCLSA2
            /note=
"synthetic DNA; synthetic linker for
            recloning
of the shortened PDGF-B precursor
            from pMVW
-2 in bacteriophage M13mp19"

(xi) SEQUENCE DESCRIPTION: SEQ
ID NO: 9:

TCGACGGGAT CGATTGGGC

19

(2) INFORMATION FOR SEQ ID NO: 10:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..37
        (D) OTHER INFORMATION:
/label= PDGBBCL
        /note=
"synthetic DNA; mutagenesis primer for
            the inser
tion of a BclI-cleavage site into the
            5'-region
 of the PDGF-B precursor"

(xi) SEQUENCE DESCRIPTION: SEQ ID NO: 10:

GCTTTATGAG ATGCTGAGTG ATCACTCGAT CCGCTCC

37

(2) INFORMATION FOR SEQ ID NO: 11:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..110
        (D) OTHER INFORMATION:
/label= PPDGFB1
        /note=
"synthetic DNA; synthetic linker for
            reconstituti
on of the mature PDGF-B
            precursor
sequence"

(xi) SEQUENCE DESCRIPTION: SEQ ID NO: 11:

TCGACACCAT GAATCGCTGC TGGGCGCTCT TCCTGTCTCT CTGCTGCTAC CT
GCGTCTGG       60

TCAGCGCCGA GGGGGACCCC ATTCCCGAGG AGCTTTATGA GATGCTGAGT
            110

(2) INFORMATION FOR SEQ ID NO: 12:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..110
        (D) OTHER INFORMATION:
/label= PPDGFB2
        /note=
"synthetic DNA; synthetic linker for
            reconstituti
on of the mature PDGF-B precursor sequence"

(xi) SEQUENCE DESCRIPTION: SEQ ID NO: 12:

GATCACTCAG CATCTCATAA AGCTCCTCGG GAATGGGGTC CCCCTCGGCG CT
GACCAGAC        60

GCAGGTAGCA GCAGAGAGAC AGGAAGAGCG CCCAGCAGCG ATTCATGGTG
            110

(2) INFORMATION FOR SEQ ID NO: 13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..30
        (D) OTHER INFORMATION: /label= 5'-POLIO1
            /note= "synthetic DNA; synthetic
            PCR primer"

(xi) SEQUENCE DESCRIPTION: SEQ ID NO: 13:

TTTCTGCAGA AGCTTAAAAC AGCTCTGGGG
            30

(2) INFORMATION FOR SEQ ID NO: 14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..28
        (D) OTHER INFORMATION: /label= 3'-POLIO2
            /note= "synthetic DNA; synthetic
            PCR primer"

(xi) SEQUENCE DESCRIPTION: SEQ ID NO: 14:

TTGCGGCCGC AATCCAATTC GCTTTATC
            28

(2) INFORMATION FOR SEQ ID NO: 15:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..13
        (D) OTHER INFORMATION:

-continued

```
/label= E-N-E1
        /note=
"synthetic DNA; synthetic linker"

(xi) SEQUENCE DESCRIPTION: SEQ
ID NO: 15:

AATTGCGGCC GCG

13

(2) INFORMATION FOR SEQ ID NO: 16:

(i) SEQUENCE CHARACTERISTICS:
        (A) LENGTH: 13 base
pairs
        (B) TYPE: nucleic acid
        (C) STRANDEDNESS: single
        (D) TOPOLOGY: linear (ix) FEATURE:
        (A) NAME/KEY: -
        (B) LOCATION: 1..13
        (D) OTHER INFORMATION:
/label= E-N-E2
        /note=
"synthetic DNA; synthetic linker"

(xi) SEQUENCE DESCRIPTION: SEQ
ID NO: 16:

AATTCGCGGC CGC

13
```